US011912982B2

(12) United States Patent
Issa et al.

(10) Patent No.: US 11,912,982 B2
(45) Date of Patent: Feb. 27, 2024

(54) METHODS FOR HPLC ANALYSIS

(71) Applicant: ModernaTX, Inc., Cambridge, MA (US)

(72) Inventors: William Issa, Dedham, MA (US); Meredith Packer, Waltham, MA (US)

(73) Assignee: ModernaTX, Inc., Cambridge, MA (US)

( * ) Notice: Subject to any disclaimer, the term of this patent is extended or adjusted under 35 U.S.C. 154(b) by 251 days.

(21) Appl. No.: 16/639,305

(22) PCT Filed: Aug. 17, 2018

(86) PCT No.: PCT/US2018/046993
§ 371 (c)(1),
(2) Date: Feb. 14, 2020

(87) PCT Pub. No.: WO2019/036685
PCT Pub. Date: Feb. 21, 2019

(65) Prior Publication Data
US 2021/0163919 A1    Jun. 3, 2021

Related U.S. Application Data

(60) Provisional application No. 62/547,647, filed on Aug. 18, 2017.

(51) Int. Cl.
*C12N 15/10* (2006.01)
*G01N 30/02* (2006.01)
*G01N 30/88* (2006.01)

(52) U.S. Cl.
CPC ............ *C12N 15/101* (2013.01); *G01N 30/02* (2013.01); *G01N 2030/8827* (2013.01); *G01N 2496/00* (2013.01)

(58) Field of Classification Search
CPC .. C12N 15/101; C12N 15/1006; G01N 30/02; G01N 30/88; G01N 2030/8825; A61K 48/0091
USPC ...................................................... 536/25.4
See application file for complete search history.

(56) References Cited

U.S. PATENT DOCUMENTS

| | | | |
|---|---|---|---|
| 6,022,715 A | 2/2000 | Merenkova et al. | |
| 6,100,024 A | 8/2000 | Hudson et al. | |
| 6,969,587 B2 * | 11/2005 | Taylor ...................... | B01J 41/20 536/25.4 |
| 7,135,289 B2 | 11/2006 | Tayler et al. | |
| 8,383,340 B2 * | 2/2013 | Ketterer ............... | C12N 15/101 536/25.4 |
| 8,710,200 B2 | 4/2014 | Schrum et al. | |
| 8,754,062 B2 | 6/2014 | De Fougerolles et al. | |
| 8,822,663 B2 | 9/2014 | Schrum et al. | |
| 8,980,864 B2 | 3/2015 | Hoge et al. | |
| 8,999,380 B2 | 4/2015 | Bancel et al. | |
| 9,221,891 B2 | 12/2015 | Bancel et al. | |
| 9,283,287 B2 | 3/2016 | Bancel et al. | |
| 9,303,079 B2 | 4/2016 | Bancel et al. | |
| 9,464,124 B2 | 10/2016 | Bancel et al. | |
| 9,512,456 B2 | 12/2016 | Wang et al. | |
| 9,533,047 B2 | 1/2017 | de Fougerolles et al. | |
| 9,572,896 B2 | 2/2017 | Bancel et al. | |
| 9,597,380 B2 | 3/2017 | Chakraborty et al. | |
| 9,675,668 B2 | 6/2017 | Bancel et al. | |
| 9,868,691 B2 | 1/2018 | Benenato et al. | |
| 9,872,900 B2 | 1/2018 | Ciaramella et al. | |
| 10,023,626 B2 | 7/2018 | Bolen et al. | |
| 10,064,934 B2 | 9/2018 | Ciaramella et al. | |
| 10,064,935 B2 | 9/2018 | Ciaramella et al. | |
| 10,124,055 B2 | 11/2018 | Ciaramella et al. | |
| 10,207,010 B2 | 2/2019 | Besin et al. | |
| 10,232,055 B2 | 3/2019 | Kariko et al. | |

(Continued)

FOREIGN PATENT DOCUMENTS

| | | |
|---|---|---|
| EP | 2092064 B1 | 9/2010 |
| WO | WO 2005/118857 A2 | 12/2005 |

(Continued)

OTHER PUBLICATIONS

International Search Report and Written Opinion for Application No. PCT/US2018/046993 dated Dec. 18, 2018.
[No Author Listed], MEGAscript Kit Product Manual, Oct. 27, 2009. Ambion/Invitrogen website: http://lools.invitrogen.com/contenl/sfs/manuals/ cms_072987.pdf, (last accessed Mar. 17, 2013).
[No Author Listed], Oligotex Handbook, Qiagen, Jun. 2012 [retrieved from internet on Sep. 22, 2020] https://www.qiagen.com/au/resources/resourcedetail?id=f9fa1d98-d54d-47e7-a20b-8b0cb8975009&lang=en.
Andrews-Pfannkoch et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.

(Continued)

*Primary Examiner* — Ganapathy Krishnan
(74) *Attorney, Agent, or Firm* — Wolf, Greenfield & Sacks, P.C.

(57) ABSTRACT

Aspects of the disclosure relate to liquid chromatography (e.g., HPLC) methods which enable high resolution separations of polynucleotides having hydrophobic portions (e.g., polyadenylated nucleic acids, such as mRNA) based upon the hydrophobic character of the molecules (e.g., polyA tail length). In some embodiments, the disclosure describes liquid chromatographic methods for separating a nucleic acid having a hydrophobic portion (e.g., a polyadenylated nucleic acid, such as an mRNA) from a complex mixture by a mobile phase system that comprises an ion pairing agent selected from Tris, inorganic cations (including e.g., Na, Li, K, ammonium, etc.), biological buffers (e.g., MOPS, HEPES, PIPES, etc.), and other charged or hydrophilic moieties, and lacks conventional ion pairing agents (e.g., Triethylammonium acetate, TEAA). Accordingly, in some embodiments methods described by the disclosure are useful for assessing the quality of pharmaceutical preparations comprising nucleic acids.

20 Claims, 13 Drawing Sheets

(56) References Cited

U.S. PATENT DOCUMENTS

| | | | |
|---|---|---|---|
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,174,500 B2 | 11/2021 | Parella et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 11,576,961 B2 | 2/2023 | Ciaramella et al. |
| 11,643,441 B1 | 5/2023 | Ciaramella et al. |
| 11,696,946 B2 | 7/2023 | Ciaramella |
| 2002/0003109 A1 | 1/2002 | Gjerde et al. |
| 2008/0220471 A1 | 9/2008 | Davis et al. |
| 2010/0048883 A1 | 2/2010 | Ketterer et al. |
| 2013/0102034 A1 | 4/2013 | Schrum et al. |
| 2013/0236974 A1 | 9/2013 | De Fougerolles |
| 2013/0245103 A1 | 9/2013 | de Fougerolles et al. |
| 2013/0259923 A1 | 10/2013 | Bancel et al. |
| 2014/0142290 A1 | 5/2014 | Madden et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0194368 A1 | 7/2016 | Hoge et al. |
| 2016/0243221 A1 | 8/2016 | Hoge et al. |
| 2016/0369243 A1* | 12/2016 | Kariko .................. A61P 25/28 |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0251754 A1 | 9/2018 | DeRosa et al. |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0125839 A1 | 5/2019 | Frederick et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0338004 A1 | 10/2020 | Hansson et al. |
| 2020/0368162 A1 | 11/2020 | Martini |
| 2021/0046173 A1 | 2/2021 | Ciaramella et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0062408 A1 | 3/2022 | Kramarczyk et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0142529 A1 | 5/2023 | White et al. |
| 2023/0181481 A1 | 6/2023 | White et al. |
| 2023/0190761 A1 | 6/2023 | Brader et al. |
| 2023/0212645 A1 | 7/2023 | Marquardt et al. |

FOREIGN PATENT DOCUMENTS

| | | | |
|---|---|---|---|
| WO | WO 2008/077592 A1 | 7/2008 | |
| WO | WO 2011/071931 A2 | 6/2011 | |
| WO | WO 2014/140211 A1 | 9/2014 | |
| WO | WO 2014/152966 A1 | 9/2014 | |
| WO | WO 2014/159813 A1 | 10/2014 | |
| WO | WO 2015/164773 A1 | 10/2015 | |
| WO | WO 2016/051170 A1 | 4/2016 | |
| WO | WO 2016/164762 A1 | 10/2016 | |
| WO | WO 2016/193206 A1 * | 12/2016 | ............ C12N 15/10 |
| WO | WO 2016/201377 A1 | 12/2016 | |
| WO | WO 2017/011773 A2 | 1/2017 | |
| WO | WO 2017/015457 A1 | 1/2017 | |
| WO | WO 2017/066789 A1 | 4/2017 | |
| WO | WO 2017/070601 A1 | 4/2017 | |
| WO | WO 2017/182524 A1 | 4/2017 | |
| WO | WO 2017/112865 A1 | 6/2017 | |
| WO | WO 2017/127750 A1 | 7/2017 | |

(56) References Cited

FOREIGN PATENT DOCUMENTS

| | | |
|---|---|---|
| WO | WO 2017/201333 A1 | 11/2017 |
| WO | WO 2018/096179 A1 | 5/2018 |
| WO | WO 2018/157009 A1 | 8/2018 |
| WO | WO 2018/232355 A1 | 12/2018 |
| WO | WO 2018/232357 A1 | 12/2018 |
| WO | WO 2019/036683 A1 | 2/2019 |
| WO | WO 2019/092153 A1 | 5/2019 |
| WO | WO 2020/097509 A1 | 11/2019 |
| WO | WO 2020/061367 A1 | 3/2020 |
| WO | WO 2020/165158 A1 | 8/2020 |
| WO | WO 2020/190750 A1 | 9/2020 |
| WO | WO 2020/232371 A1 | 11/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/155274 A1 | 8/2021 |
| WO | WO 2021/159040 A2 | 8/2021 |
| WO | WO 2021/159130 A2 | 8/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/247817 A1 | 12/2021 |
| WO | WO 2022/032154 A2 | 2/2022 |
| WO | WO 2022/067010 A1 | 3/2022 |
| WO | WO 2022/204491 A1 | 9/2022 |
| WO | WO 2023/092069 A1 | 5/2023 |
| WO | WO 2023/107999 A2 | 6/2023 |
| WO | WO 2023/114307 A1 | 6/2023 |
| WO | WO 2023/132885 A1 | 7/2023 |
| WO | WO 2023/137149 A1 | 7/2023 |

OTHER PUBLICATIONS

Dickman et al., Ion Pair Reverse-Phase Chromatography: A Versatile Platform for the Analysis of RNA. Chromatography Today. 2011; 22-26.

Easton et al., Rapid, nondenaturing RNA purification using weak anion-exchange fast performance liquid chromatography. RNA. Mar. 2010;16(3):647-53. Epub Jan. 25, 2010.

Georgopoulos et al., Use of high-performance liquid chromatographic fractionation of large RNA molecules in the assay of group I intron ribozyme activity. J Chromatogr A. Jan. 28, 2000;868(1):109-14.

Huber et al., Analysis of nucleic acids by on-line liquid chromatography—Mass spectrometry (Mass Spectrometry Reviews 2001, 20, pp. 310-343).

Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.

Kariko et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.

Kingston, 'Preparation of poly (A)+ RNA', Current protocols in molecular biology. 1993, vol. 21, No. 1, pp. 4.51-4.5.3.

Koch et al., Quantitative Studies on the Infectivity of ribonucleic acid from partially purified and highly purified poliovirus preparations. Virology. Mar. 1960; 10(3): 329-343.

Lee et al., Separation and determination of polyethylene glycol fatty acid esters in cosmetics by a reversed-phase HPLC/ELSD. Talanta. Feb. 15, 2008;74(5):1615-20. doi: 10.1016/j.talanta.2007.10.020. Epub Oct. 18, 2007.

Lewandowski et al., Separation of the infectious ribonucleic acid of potato spindle tuber virus from double-stranded ribonucleic acid of plant tissue extracts. J Virol. Nov. 1971;8(5):809-12.

Mellits et al., Removal of double-stranded contaminants from RNA transcripts: synthesis of adenovirus VA RNAI from a T7 vector. Nucleic Acids Res. Sep. 25, 1990;18(18):5401-6.

Mignone et al., Untranslated regions of mRNAs. Genome Biol. 2002;3(3):REVIEWS0004. Epub Feb. 28, 2002. pp. 1-10.

Nwokeoji et al., Purification and characterisation of dsRNA using ion pair reverse phase chromatography and mass spectrometry. J Chromatogr A. Feb. 10, 2017;1484:14-25. doi: 10.1016/j.chroma.2016.12.062. Epub Dec. 21, 2016.

Slater, The purification of poly(a)-containing RNA by affinity chromatography. Methods Mol Biol. 1985;2:117-20. doi: 10.1385/0-89603-064-4:117.

Wang et al., Purification of the messenger ribonucleic acid for the lipoprotein of the *Escherichia coli* outer membrane. Biochemistry. Oct. 2, 1979;18(20):4270-7.

Weissman et al., HPLC purification of in vitro transcribed long RNA. Methods Mol Biol. 2013;969:43-54. doi: 10.1007/978-1-62703-260-5_3.

Wysoczynski et al., Reversed-phase ion-pair liquid chromatography method for purification of duplex DNA with single base pair resolution. Nucleic Acids Res. Nov. 2013;41(20):e194. doi: 10.1093/nar/gkt815. Epub Sep. 5, 2013.

Azarani et al., RNA analysis by ion-pair reversed-phase high performance liquid chromatography. Nucleic Acids Res. Jan. 15, 2001;29(2):E7. doi: 10.1093/nar/29.2.e7.

Buszewski et al., Hydrophilic interaction liquid chromatography (HILIC)—a powerful separation technique. Anal Bioanal Chem. Jan. 2012;402(1):231-47. doi: 10.1007/s00216-011-5308-5. Epub Aug. 31, 2011.

Dickman et al., Enrichment and analysis of RNA centered on ion pair reverse phase methodology. RNA. Apr. 2006;12(4):691-6. doi: 10.1261/rna.2278606. Epub Feb. 22, 2006.

Gjerde et al., RNA Purification and Analysis: Sample Preparation, Extraction, Chromatography. Appendix 2: "HPLC Instumentation and Operation." Wiley-VCH Verlag GmbH & Co. KGaA, Weinheim ISBN: 978-3-527-32116-2 (Year: 2009). pp. 159-183.

Gong et al., Comparing ion-pairing reagents and sample dissolution solvents for ion-pairing reversed-phase liquid chromatography/electrospray ionization mass spectrometry analysis of oligonucleotides. Rapid Commun Mass Spectrom. Feb. 28, 2014;28(4):339-50. doi: 10.1002/rcm.6773.

Gong, Comparing ion-pairing reagents and counter anions for ion-pair reversed-phase liquid chromatography/electrospray ionization mass spectrometry analysis of synthetic oligonucleotides.Rapid Commun Mass Spectrom. Dec. 30, 2015;29(24):2402-10. doi: 10.1002/rcm.7409.

Holzl et al., Analysis of biological and synthetic ribonucleic acids by liquid chromatography-mass spectrometry using monolithic capillary columns. Anal Chem. Jan. 15, 2005;77(2):673-80. doi: 10.1021/ac0487395.

Huang et al., Development of simple isocratic HPLC methods for siRNA quantitation in lipid-based nanoparticles. J Pharm Biomed Anal. Aug. 5, 2019;172:253-258. doi: 10.1016/j.jpba.2019.04.026. Epub Apr. 27, 2019.

Jora et al., Detection of ribonucleoside modifications by liquid chromatography coupled with mass spectrometry. Biochim Biophys Acta Gene Regul Mech. Mar. 2019;1862(3):280-290. doi: 10.1016/j.bbagrm.2018.10.012. Epub Nov. 7, 2018.

Li et al., Simultaneous separation of small interfering RNA and lipids using ion-pair reversed-phase liquid chromatography. J Chromatogr A. Sep. 13, 2019;1601:145-154. doi: 10.1016/j.chroma.2019.04.061. Epub Apr. 27, 2019.

Lobue et al., Oligonucleotide analysis by hydrophilic interaction liquid chromatography-mass spectrometry in the absence of ion-pair reagents. J Chromatogr A. Jun. 21, 2019;1595:39-48. doi: 10.1016/j.chroma.2019.02.016. Epub Feb. 7, 2019.

Mccarthy et al., Hexylammonium Acetate as an Ion-Pairing Agent for IP-RP LC Analysis of Oligonucleotides. Application Note. Waters. 2016. pp. 1-15.

Murugaiah et al., Reversed-phase high-performance liquid chromatography method for simultaneous analysis of two liposome-

(56) References Cited

OTHER PUBLICATIONS formulated short interfering RNA duplexes. Anal Biochem. Jun. 1, 2010;401(1):61-7. doi: 10.1016/j.ab.2010.02.012. Epub Feb. 13, 2010.

Shibue et al., Effect of anionic ion-pairing reagent concentration (1-60 mM) on reversed-phase liquid chromatography elution behaviour of peptides. J Chromatogr A. Jul. 1, 2005;1080(1):58-67. doi: 10.1016/j.chroma.2005.02.047.

Stahlberg et al., Chromatography: Liquid II Ion Pair Liquid Chromatography. Editor(s): Ian D. Wilson, Encyclopedia of Separation Science, Academic Press, 2000, pp. 676-684.

Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.

Zhang et al., Ion-pair reversed-phase chromatography of short double-stranded deoxyribonucleic acid in silicon micro-pillar array columns: retention model and applications. J Chromatogr A. Jun. 14, 2013;1294:1-9. doi: 10.1016/j.chroma.2013.04.002. Epub Apr. 8, 2013.

* cited by examiner

METHODS FOR HPLC ANALYSIS

RELATED APPLICATIONS

The present application is a national stage filing under 35 U.S.C. § 371 of international PCT application, PCT/US2018/046993, filed Aug. 17, 2018, which claims priority under 35 U.S.C. § 119(e) to U.S. provisional patent application, U.S. Ser. No. 62/547,647, filed Aug. 18, 2017, the entire contents of each of which are incorporated herein by reference.

BACKGROUND

Messenger RNA (mRNA) molecules can be produced for therapeutic or prophylactic use in humans. For example, an mRNA containing a therapeutic and/or prophylactic gene of interest, 5' and 3' untranslated regions (UTRs) and a 3' polyadenylated tail (polyA tail) of a defined length can be generated from a double-stranded DNA template via in vitro transcription (IVT). An appropriate 5' cap and 3' polyA tail are thought to be required for effective translation of the encoded protein by cellular machinery, directly impacting potency, and are therefore both considered critical quality attributes of mRNA drug substances.

Tailless mRNA species of various lengths can be generated throughout the transcription process and may include, for example, abortive transcripts, off-target IVT products, and strand scission degradation products. Tail length variants primarily originate from DNA template with a heterogeneous tail population, but may also be products of degradation or incomplete transcription.

SUMMARY

In some aspects, the disclosure relates to gradient-based reversed phase HPLC methods for separating, e.g., selectively separating, polynucleotides (e.g., RNAs, for example mRNAs) comprising one or more hydrophobic portions. Thus, in some embodiments, methods described by the disclosure are useful for polyA tail length-based separation of intact mRNA from complex mixtures. The disclosure is based, in part, on the discovery of inclusion of certain molecules (e.g., tris(hydroxymethyl)aminomethane ("Tris"), inorganic cations including e.g., Na, Li, K, ammonium, etc., biological buffers such as MOPS, HEPES, PIPES, and other charged or hydrophilic moieties) in a mobile phase lacking other ion pairing agents allows for separation and/or quantification of nucleic acids within a complex mixture (e.g., the tailless mRNA population within a polyadenylated mRNA preparation, identification of the presence of tail truncates or secondary populations of different tail lengths, etc.) based upon the hydrophobic character of the molecules being separated.

Accordingly, in some aspects, the disclosure provides a method for separating a nucleic acid having a hydrophobic portion (e.g., a polyadenylated nucleic acid such as mRNA) from a mixture comprising one or more additional nucleic acids or impurities, the method comprising: contacting a stationary phase of a reverse phase chromatography column with a mixture; and eluting the nucleic acid having a hydrophobic portion (e.g., a polyadenylated nucleic acid) with a mobile phase, wherein the mobile phase comprises an ion pairing agent selected from Tris, inorganic cations (including e.g., Na, Li, K, ammonium, etc.), biological buffers (e.g., MOPS, HEPES, PIPES, etc.), and other charged or hydrophilic moieties and lacks other ion pairing agents, such that the nucleic acid having a hydrophobic portion (e.g., polyadenylated nucleic acid) traverses the column with a retention time that is different than the one or more other nucleic acids of the mixture.

In some embodiments, the column is an analytical column. In some embodiments, the column has a temperature from about 20° C. to about 100° C. In some embodiments, the column has a temperature from about 70° C. to about 90° C., optionally wherein the column has a temperature of about 80° C.

In some embodiments, the stationary phase is hydrophobic. In some embodiments, the stationary phase comprises particles. In some embodiments, the particles are porous resin particles. In some embodiments, particles are hydrophobic (e.g., comprise an intrinsically hydrophobic material such as polystyrene divinylbenzene) or comprise hydrophobic functional groups. In some embodiments, the particles have a diameter of about 2 µm-about 10 µm, about 2 µm-about 6 µm, or about 4 µm. In some embodiments, the particles comprise pores having a diameter of about 500 Å to about 10,000 Å, about 800 Å to about 3000 Å, or about 1000 Å to about 2000 Å.

In some embodiments, the nucleic acid having a hydrophobic portion is a polyadenylated nucleic acid, such as mRNA. In some embodiments, the mRNA is in vitro transcribed (IVT) mRNA. In some embodiments, the polyadenylated nucleic acid comprises a polyA tail between about 10 and 500 adenosine monophosphates in length, about 20 and about 200 adenosine monophosphates in length, or about 30 to 120 adenosine monophosphates in length. In some embodiments, the polyadenylated nucleic acid comprises a polyA tail between about 100 and 1000 adenosine monophosphates in length. In some embodiments, the polyadenylated nucleic acid has a total length of between about 100 nucleotides and about 10,000 nucleotides, about 100 nucleotides to about 5,000 nucleotides, or about 200 nucleotides to about 4,000 nucleotides. In some embodiments, the mRNA is intact mRNA (e.g., mRNA that has not been enzymatically digested).

In some embodiments, the mixture comprises one or more tail length variants. In some embodiments, the mixture comprises one or more degradation products.

In some embodiments, the mobile phase is a single solvent. In some embodiments, the mobile phase is a mixture of a first solvent and a second solvent. In some embodiments, the mobile phase is a mixture of a first solvent solution and a second solvent solution.

In some embodiments, the volume percentage of the first solvent solution in the mobile phase is 0% to 100% (e.g., any percentage between 0% (absent) and 100%, inclusive). In some embodiments, the first solvent solution comprises an ion pairing agent selected from Tris, inorganic cations (including e.g., Na, Li, K, ammonium, etc.), biological buffers (e.g., MOPS, HEPES, PIPES, etc.), and other charged or hydrophilic moieties. In some embodiments, the concentration of the ion pairing agent in the first solvent solution ranges from about 1 mM-200 mM, 5 mM-200 mM, 5 mM-75 mM, 5 mM-50 mM, 5 mM-25 mM, 5 mM-10 mM, 10 mM-25 mM, 25 mM-50 mM, 25 mM-75 mM, 50 mM-100 mM or 75 mM-100 mM. In some embodiments, the first solvent solution further comprises a chelator (e.g., EDTA), optionally wherein the concentration of the chelator (e.g. EDTA) ranges from about 1 mM to about 5 mM. In some embodiments, the concentration of EDTA is about 2.5 mM.

In some embodiments, the volume percentage of the second solvent solution in the mobile phase is 0% to 100%.

In some embodiments, the second solvent solution comprises Tris. In some embodiments, the concentration of ion pairing agent (e.g., Tris, inorganic cations (including e.g., Na, Li, K, ammonium, etc.), biological buffers (e.g., MOPS, HEPES, PIPES, etc.), and other charged or hydrophilic moieties) in the second solvent solution ranges from about 1 mM-200 mM, 5 mM-200 mM, 5 mM-75 mM, 5 mM-50 mM, 5 mM-25 mM, 5 mM-10 mM, 10 mM-25 mM, 25 mM-50 mM, 25 mM-75 mM, 50 mM-100 mM or 75 mM-100 nM. In some embodiments, the second solvent solution further comprises a chelator (e.g., EDTA), optionally wherein the concentration of chelator (e.g., EDTA) ranges from about 1 mM to about 5 mM. In some embodiments, the concentration of EDTA is about 2.5 mM.

In some embodiments, the first solvent solution and/or second solvent solution comprises an organic solvent selected from the group consisting of water, polar aprotic solvents (including, e.g., tetrahydrofuran (THF), dimethyl sulfoxide (DMSO), dimethylformamide (DMF), acetonitrile, acetone, etc.), C1-4 alkanols, C1-6 alkandiols, and C2-4 alkanoic acids. In some embodiments, the first solvent solution and/or second solvent solution comprises one or more solvents selected from the group consisting of water, acetonitrile, methanol, ethanol, isopropanol, hexylene glycol, and acetic acid.

In some embodiments, the pH of the mobile phase is between about pH 6.8 and pH 8.5, optionally wherein the pH is about 7.0. In some embodiments, the pH of the first solvent solution is between about pH 6.8 and pH 8.5, optionally wherein the pH is about 7.0. In some embodiments, the pH of the second solvent solution is between about pH 6.8 and pH 8.5, optionally wherein the pH is about 7.0.

In some embodiments of HPLC methods described by the disclosure, the eluting is gradient with respect to mobile phase solvent composition. In some embodiments, the eluting is isocratic with respect to the concentration of Tris in the mobile phase.

In some embodiments, HPLC methods as described by the disclosure have a run time of between about 10 minutes and about 30 minutes.

In some embodiments, HPLC methods described by the disclosure further comprise the step of detecting or isolating the polyadenylated nucleic acid.

In some aspects, the disclosure provides a pure mRNA sample comprising: a composition of an in vitro transcribed (IVT) RNA and a pharmaceutically acceptable carrier, wherein the composition comprises the polyadenylated nucleic acid separated by a HPLC method as described by the disclosure.

In some embodiments, polyA tail content measured by HPLC methods described by the disclosure is indicative of mRNA potency. Thus, in some aspects, the disclosure provides a method of quality control of a pharmaceutical composition comprising a nucleic acid having a hydrophobic portion (e.g., a polyadenylated nucleic acid, such as an intact mRNA), the method comprising: separating a nucleic acid having a hydrophobic portion from a mixture comprising one or more additional nucleic acids or impurities by a HPLC method as described herein; comparing the separated nucleic acid with a reference nucleic acid; and determining the nucleic acid has a desired hydrophobic character (e.g., has a full length polyA tail or comprises a desired hydrophobic base modification) based on a comparison of the separated nucleic acid with the reference polyadenylated nucleic acid. In some embodiments, the determining step further comprises quantifying an amount of nucleic acid having a reduced hydrophobic character in the composition (e.g., polyadenylated nucleic acids having no or shortened polyA tails). In some embodiments, the ratio of tailless nucleic acid to tailed nucleic acid in a mixture is indicative of the stability of the pharmaceutical composition and in turn the potency.

In some embodiments, the comparing step comprises comparing a HPLC chromatogram of the separated polyadenylated nucleic acid with a HPLC chromatogram of the reference polyadenylated nucleic acid. In some embodiments, the method further comprises comparing the nucleic acid separated from the mixture with a reference nucleic acid using an analytical method, for example polymerase chain reaction (e.g., qRT-PCR), nucleic acid sequencing, gel electrophoresis, restriction digest-based analysis, mass spectrometry, etc.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

FIG. 10 shows representative data for the effect of run temperature on observed % tailed. There is some trend towards lower observed % tailed with increasing temperature, but the differences were generally within 3%. The gradient was not adjusted to normalize retention time, which shifts earlier at higher temperatures, resulting in a shorter residence time. At 95° C. and 100° C., the tailless peak begins to shift to the flow-through.

DETAILED DESCRIPTION

Figure 1:
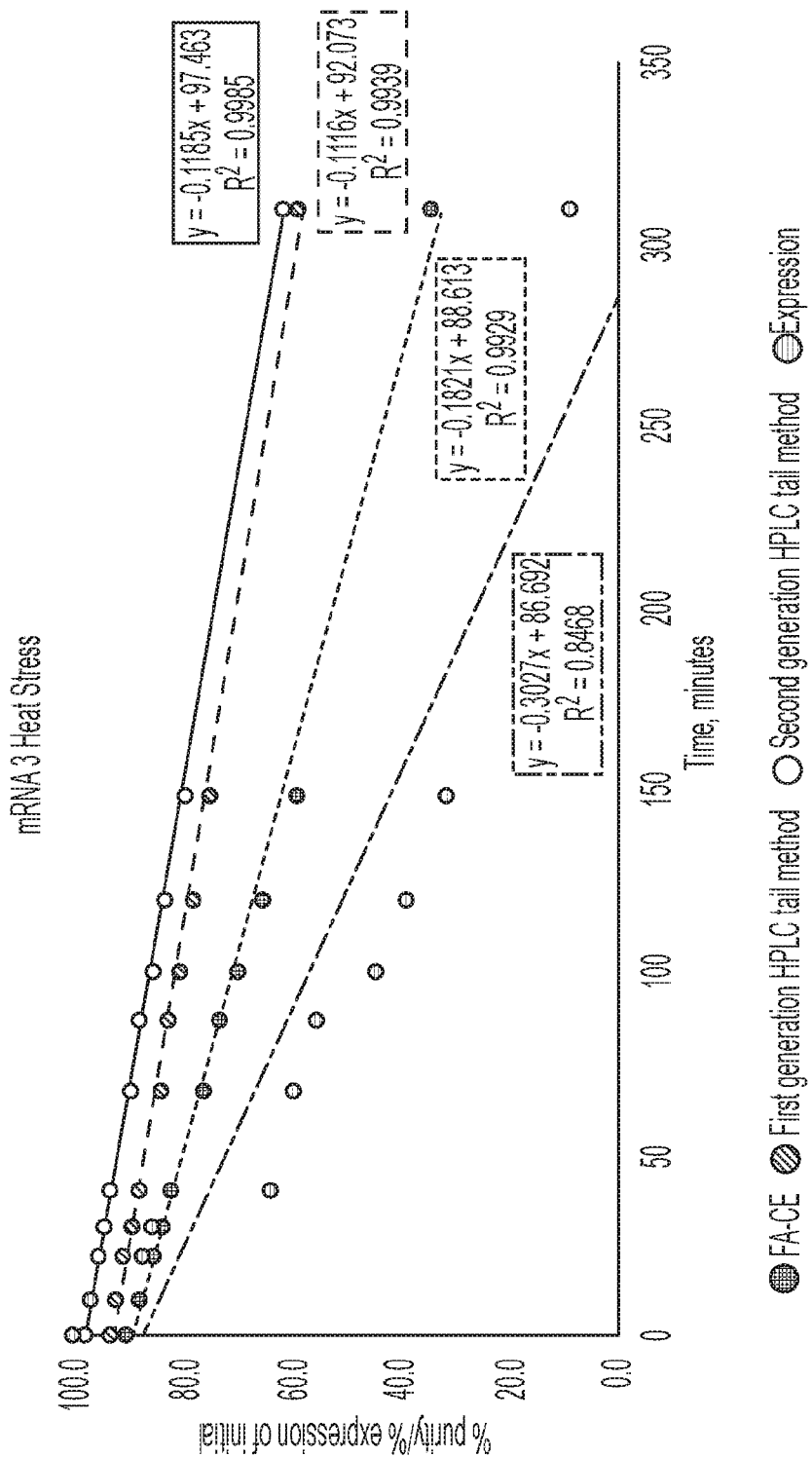
FIG. 1 shows a representative histogram measuring heat-stress degradation by impurity quantitation and expression in HeLa cells. Time points along a heat degradation series of mRNA 3 were analyzed by both generations of the HPLC tail assay, FA-CE, and in vitro expression. The tailless degradation products only make up a portion of the total nonfunctional material, so both generations of the tail method have shallower slopes than the FA separation by length. The two generations of the HPLC tail method show equivalent slopes (indicating rate of formation of tailless species), and the higher overall value at each point is indicative of less in-run degradation in the second generation method.

In some aspects, the disclosure relates to high performance liquid chromatography methods (e.g., HPLC methods) for analyzing polynucleotides (e.g., mixtures containing polynucleotides, such as RNA molecules). Typically, an HPLC apparatus comprises a reservoir containing a mobile phase, a sample input port, a chromatography column containing the stationary phase, and a detection apparatus. HPLC apparatus and methods for HPLC detection of RNA molecules are generally described, for example in U.S. Pat. No. 8,383,340, the entire contents of which are incorporated herein by reference.

In some aspects, the disclosure relates to reversed phase HPLC (RP HPLC). Generally, RP HPLC refers to a liquid chromatographic methodology. RP HPLC methods typically use a single ion pairing agent (e.g., an anionic ion pairing agent, such as triethylammonium acetate, "TEAA") to increase retention time or resolution of nucleic acids.

Without wishing to be bound by any particular theory, in some embodiments, the hydrophobic character-based (e.g., polyA tail length-based) selectivity described by HPLC methods of the disclosure relates to the intrinsic hydrophobicity of adenosine nucleobases and/or certain hydrophobic nucleobase modifications (e.g., 2'-O-methyl, 2'OMe) compared to the other nucleobases. For example, the long stretch of adenosines at the 3' end of polyadenylated nucleic acids (e.g., mRNA) acts as a hydrophobic tag, increasing retention in a reversed phase HPLC system. In another example, one or more nucleobase modifications increases the hydrophobic character of a nucleic acid and acts as a hydrophobic tag. Other examples of hydrophobic tags include but are not limited to certain linkers, dyes, conjugates, cargo molecules, polyethylene glycol polymers (PEG), GalNAc, etc. The disclosure is based, in part, on the discovery that using certain ion pairing agents, (e.g., tris(hydroxymethyl)aminomethane ("Tris"), inorganic cations (including e.g., Na, Li, K, ammonium, etc.), biological buffers (e.g., MOPS, HEPES, PIPES, etc.), and other charged or hydrophilic moieties) as a counterion in the absence of other ion pairing agents (e.g., triethylamine or salts (e.g., ammonium salts) thereof (e.g., TEAA), dibutylamine or salts (e.g., ammonium salts) thereof (e.g., DBAA), hexylamine or salts (e.g., ammonium salts) thereof (e.g., hexylammonium acetate, HAA), etc.) during HPLC contributes very little to the overall hydrophobicity of sample molecules (e.g., mRNA) compared to more traditional hydrophobic alkyl chain ion pairs (e.g., quaternary amine ion pairing agents, such as TEA, etc.) and therefore selectivity of HPLC methods described herein is driven almost exclusively by the hydrophobic character (e.g., polyA tail length) of the sample molecules.

As used herein, a "nucleic acid with a hydrophobic portion" refers to a portion of the polynucleotide (e.g., one or more contiguous, for example covalently connected, nucleotides) which is more hydrophobic than other portions of the polynucleotide, owing to the presence of several hydrophobic (e.g., non-polar) nucleotides (e.g., unmodified hydrophobic nucleobases such as adenosine monophosphate, or nucleobases that have been modified with a hydrophobic moiety, for example 2'OMe). In some embodiments, a hydrophobic portion comprises at least 5, at least 10, at least 20, at least 50, at least 100, at least 1000, or more hydrophobic nucleotides. In some embodiments, a hydrophobic portion comprises between 20 and 200 hydrophobic nucleotides, e.g., between 20 and 100 hydrophobic nucleotides or between 20 and 50 hydrophobic nucleotides. In some embodiments, a hydrophobic portion is preferably an end (e.g., terminal) portion, e.g., a 5' or 3' end of a polynucleotide. In some embodiments, a hydrophobic portion is in an untranslated region (UTR) of a polynucleotide.

Accordingly, in some aspects, the disclosure provides a method for separating a nucleic acid having a hydrophobic portion (e.g., a polyadenylated nucleic acid) from a mixture comprising one or more additional nucleic acids or impurities, the method comprising: contacting a stationary phase of a reverse phase chromatography column with a mixture; and eluting the nucleic acid with a mobile phase, wherein the mobile phase comprises an ion pairing agent selected from Tris, inorganic cations (including e.g., Na, Li, K, ammonium, etc.), biological buffers (e.g., MOPS, HEPES, PIPES, etc.), and other charged or hydrophilic moieties, and lacks other ion pairing agents, such that the nucleic acid traverses the column with a retention time that is different than the one or more other nucleic acids of the mixture.

In some aspects, the disclosure relates to the discovery that reverse phase HPLC mobile phases that include certain unconventional ion pairing agents, (e.g., Tris, inorganic cations (including e.g., Na, Li, K, ammonium, etc.), biological buffers (e.g., MOPS, HEPES, PIPES, etc.), and other charged or hydrophilic moieties) and lack conventional ion pairing agents (e.g., triethylammonium salts, tetrabutylammonium salts, hexylammonium salts and dibutylammonium salts, etc.) enable polyA tail length-based separation of nucleic acids from complex mixtures.

As used herein, an "ion pairing agent" or an "ion pair" refers to an agent (e.g., a small molecule) that functions as a counter ion to a charged (e.g., ionized or ionizable) functional group on an HPLC analyte (e.g., a nucleic acid) and thereby changes the retention time of the analyte as it moves through the stationary phase of an HPLC column. Generally, ion paring agents are classified as cationic ion pairing agents (which interact with negatively charged functional groups) or anionic ion pairing agents (which interact with positively charged functional groups). The terms "ion pairing agent" and "ion pair" further encompass an associated counter-ion (e.g., acetate, phosphate, bicarbonate, chloride, citrate, nitrate, nitrite, oxide, sulfate and the like, for cationic ion pairing agents, and sodium, calcium, and the like, for anionic ion pairing agents).

As used herein, "tris(hydroxymethyl)aminomethane" and "Tris" refer to an organic molecule having the chemical formula $(HOCH_2)_3CNH_2$ (e.g., 2-Amino-2-(hydroxymethyl)propane-1,3-diol). In some embodiments, the ion pairing agent used in methods as described by the disclosure is Tris acetate. In some embodiments, the ion pairing agent used in methods as described by the disclosure is an inorganic cation (including e.g., Na, Li, K, ammonium, etc.). In some embodiments, the ion pairing agent used in methods as described by the disclosure is a biological buffer (e.g., MOPS, HEPES, PIPES, etc.), or another charged or hydrophilic moiety. In some embodiments of methods described by the disclosure, the concentration of an ion pairing agent as described by the disclosure in a HPLC mobile phase ranges from about 1 mM to about 2 M (e.g., about 1 mM, about 2 mM, about 5 mM, about 10 mM, about 50 mM, about 100 mM, about 200 mM, about 500 mM, about 1 M, about 1.2 M, about 1.5 M, or about 2M), inclusive. In some embodiments, the concentration of an ion pairing agent ranges from about 1 mM-200 mM, 5 mM-200 mM, 5 mM-75 mM, 5 mM-50 mM, 5 mM-25 mM, 5 mM-10 mM, 10 mM-25 mM, 25 mM-50 mM, 25 mM-75 mM, 50 mM-100 mM or 75 mM-100 mM. In some embodiments of HPLC methods described by the disclosure, the mobile phase completely lacks ion pairing agents other than Tris, inorganic cations (including e.g., Na, Li, K, ammonium, etc.), biological buffers (e.g., MOPS, HEPES, PIPES, etc.), and other charged or hydrophilic moieties (e.g., other ion pairing agents are absent from the mobile phase, or solvent solutions), for example, triethylammonium acetate (TEAA), tetrabutylammonium phosphate (TBAP), hexylammonium acetate (HAA) and dibutylammonium acetate (DBAA).

In some embodiments, the mobile phase further comprises a chelating agent. Examples of chelating agents include but are not limited to ethylenediamine (EDTA), ethylene glycol-bis(β-aminoethyl ether)-N,N,N',N'-tetraacetic acid) (EGTA), phosphonate, diethylenetriamine (DETA), etc. The concentration of the chelating agent can vary. For example, in some embodiments, the concentration of chelating agent in the mobile phase ranges from about 1 mM to about 10 mM (e.g., about 1 mM, about 2 mM, about 3 mM, about 4 mM, about 5 mM, about 6 mM, about 7 mM, about 8 mM, about 9 mM, about 10 mM, or any value between).

In HPLC methods as described by the disclosure, Tris and/or chelator, such as EDTA (e.g., Tris-EDTA, also referred to as TAE) is dispersed within a mobile phase. As used herein, a "mobile phase" is an aqueous solution comprising water and/or one or more organic solvents used to carry an HPLC analyte (or analytes), such as a nucleic acid or mixture of nucleic acids through an HPLC column. Generally, a IP-RP HPLC mobile phase comprises a polar organic solvent. Examples of polar organic solvents suitable for inclusion in a mobile phase include but are not limited to alcohols, ketones, nitrates, esters, amides and alkylsulfoxides. In some embodiments, a mobile phase comprises one or more organic solvents selected from the group consisting of acetonitrile, methanol, ethanol, propanol, isopropanol, dimethylformamide, methyl acetate, acetone, and dimethyl sulfoxide (DMSO), hexaline glycol, polar aprotic solvents (including, e.g., tetrahydrofuran (THF), dimethyl sulfoxide (DMSO), dimethylformamide (DMF), acetonitrile, acetone, etc.), $C_{1-4}$ alkanols, $C_{1-6}$ alkandiols, and $C_{2-4}$ alkanoic acids. In some embodiments, a mobile phase comprises acetonitrile. In some embodiments, a mobile phase comprises additional components, for example as described in U.S. Patent Publication US 2005/0011836, the entire contents of which are incorporated herein by reference.

The concentration of organic solvent in a mobile phase can vary. For example, in some embodiments, the volume percentage (v/v) of an organic solvent in a mobile phase varies from 0% (absent) to about 100% of a mobile phase. In some embodiments, the volume percentage of organic solvent in a mobile phase is between about 5% and about 75% v/v. In some embodiments, the volume percentage of organic solvent in a mobile phase is between about 25% and about 60% v/v. In some embodiments, the concentration of organic solvent in a mobile phase is about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

In some embodiments, a mobile phase for use in HPLC methods as described by the disclosure is comprised of multiple (e.g., 2, 3, 4, 5, or more) solvent solutions. In some embodiments of HPLC methods described by the disclosure, the mobile phase comprises two solvent solutions (e.g., Mobile Phase A, and Mobile Phase B). In some embodiments, a solvent solution comprises one or more organic solvent (e.g., polar solvent, such as water and/or acetonitrile) and an ion pairing agent as disclosed herein.

The concentration of two or more solvent solutions in a mobile phase can vary. For example, in a mobile phase comprising two solvent solutions (e.g., a first solvent solution and a second solvent solution), the volume percentage of the first solvent solution may range from about 0% (absent) to about 100%. In some embodiments, the volume percentage of the first solvent solution may range from about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

Conversely, in some embodiments, the volume percentage of the second solvent solution of a mobile phase may range from about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

In some aspects, the disclosure relates to the discovery that solvent solution gradients, where the ratio of the first solvent solution (e.g., Mobile Phase A) and the second solvent solution (e.g., Mobile Phase B) is manipulated at increasing, constant, or decreasing organic composition, allow for high resolution separations of polyadenylated nucleic acids (e.g., mRNAs, such as IVT mRNAs). Thus, in some embodiments, a polyadenylated nucleic acid traverses the HPLC column with a retention time that is different than one or more other nucleic acids or impurities of a mixture.

In some embodiments, the ratio of Tris concentration in the first solvent solution to Tris concentration in the second solvent solution is held constant (e.g., isocratic) during elution of the polyadenylated nucleic acid. However, the skilled artisan will appreciate that in other embodiments, the relative ratio of Tris concentration in the first solvent solution to Tris concentration in the second solvent solution can vary throughout the elution step. For example, in some embodiments, the ratio of Tris concentration in the first solvent solution is increased relative to Tris concentration in the second solvent solution during the elution step. In some embodiments, the ratio of Tris concentration in the first solvent solution is decreased relative to Tris concentration in the second solvent solution during the elution step.

The pH of the mobile phase (e.g., the pH of each solvent solution of the mobile phase) can vary. In some embodiments, the pH of the mobile phase is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the mobile phase is between about pH 6.8 and pH 8.5 (e.g., about 6.8, about 7.0, about 7.2, about 7.4, about 7.6, about 7.8, about 8.0, about 8.3, or about 8.5). In some embodiments, the pH of the mobile phase is about 7.0.

In some embodiments, the pH of the first solvent solution is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the first solvent solution is between about pH 6.8 and pH 8.5 (e.g., about 6.8, about 7.0, about 7.2, about 7.4, about 7.6, about 7.8, about 8.0, about 8.3, or about 8.5). In some embodiments, the pH of the first solvent solution is about 7.0.

In some embodiments, the pH of the second solvent solution is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the second solvent solution is between about pH 6.8 and pH 8.5 (e.g., about 6.8, about 7.0, about 7.2, about 7.4, about 7.6, about 7.8, about 8.0, about 8.3, or about 8.5). In some embodiments, the pH of the second solvent solution is about 7.0.

Any suitable HPLC column (e.g., stationary phase) may be used in the methods described by the disclosure. Generally, a "HPLC column" is a solid structure or support that contains a medium (e.g. a stationary phase) through which the mobile phase and HPLC sample (e.g., a sample containing HPLC analytes, such as nucleic acids) is eluted. Without wishing to be bound by any particular theory, the composition and chemical properties of the stationary phase determine the retention time of HPLC analytes. In some embodiments of HPLC methods described by the disclosure, the stationary phase is non-polar. Examples of non-polar stationary phases include but are not limited to resin, silica (e.g., alkylated and non-alkylated silica), polystyrenes (e.g., alkylated and non-alkylated polystyrenes), polystyrene divinylbenzenes, etc. In some embodiments, a stationary phase comprises particles, for example porous particles. In some embodiments, a stationary phase (e.g., particles of a stationary phase) is hydrophobic (e.g., made of an intrinsically hydrophobic material, such as polystyrene divinylbenzene), or comprise hydrophobic functional groups. In some embodiments, a stationary phase is a membrane or monolithic stationary phase.

The particle size (e.g., as measured by the diameter of the particle) of an HPLC stationary phase can vary. In some embodiments, the particle size of a HPLC stationary phase ranges from about 1 µm to about 100 µm (e.g., any value between 1 and 100, inclusive) in diameter. In some embodiments, the particle size of a HPLC stationary phase ranges from about 2 µm to about 10 µm, about 2 µm to about 6 µm, or about 4 µm in diameter. The pore size of particles (e.g., as measured by the diameter of the pore) can also vary. In some embodiments, the particles comprise pores having a diameter of about 100 Å to about 10,000 Å. In some embodiments, the particles comprise pores having a diameter of about 100 Å to about 5000 Å, about 100 Å to about 1000 Å, or about 1000 Å to about 2000 Å. In some embodiments, the stationary phase comprises polystyrene divinylbenzene, for example as used in the DNAPac RP analytical column.

The temperature of the column (e.g., the stationary phase within the column) can vary. In some embodiments, the column has a temperature from about 20° C. to about 100° C. (e.g., any temperature between 20° C. and 99° C.). In some embodiments, the column has a temperature from about 40° C. to about 100° C. (e.g., any temperature between 40° C. and 99° C., for example about 40° C., about 50° C., about 60° C., about 70° C., about 80° C., about 90° C., about 95° C., or about 100° C.). In some embodiments, the column has a temperature from about 70° C. to about 90° C. (e.g., any temperature between 70° C. and 90° C.). In some embodiments, the column has a temperature of about 80° C.

In some embodiments, HPLC methods as described by the disclosure comprise the step of detecting or isolating a nucleic acid. Any detection apparatus or modality suitable for HPLC may be used. Examples of HPLC detectors include but are not limited to absorbance detectors (e.g., UV/VIS detectors), fluorescence detectors, electrochemical detectors, and mass spectrometric detectors.

In some aspects, the disclosure relates to improved HPLC methods for detection of nucleic acids. As used herein, a "polynucleotide" or "nucleic acid" is at least two nucleotides covalently linked together, and in some instances, may contain phosphodiester bonds (e.g., a phosphodiester "backbone") or modified bonds, such as phosphorothioate bonds. An "engineered nucleic acid" is a nucleic acid that does not occur in nature. In some instances the nucleic acid is an engineered nucleic acid. It should be understood, however, that while an engineered nucleic acid as a whole is not naturally-occurring, it may include nucleotide sequences that occur in nature. Thus, a "polynucleotide" or "nucleic acid" sequence is a series of nucleotide bases (also called "nucleotides"), generally in DNA and RNA, and means any chain of two or more nucleotides. The terms include genomic DNA, cDNA, RNA, any synthetic and genetically manipulated polynucleotides. This includes single- and double-stranded molecules; i.e., DNA-DNA, DNA-RNA, and RNA-RNA hybrids as well as "protein nucleic acids" (PNA) formed by conjugating bases to an amino acid backbone.

The methods of the invention involve the analysis of samples (e.g., mixtures) comprising one or more nucleic acids, for example DNA or RNA. An RNA typically is composed of repeating ribonucleosides. It is possible that the RNA includes one or more deoxyribonucleosides. In preferred embodiments the RNA is comprised of greater than 60%, 70%, 80% or 90% of ribonucleosides. In other embodiments the RNA is 100% comprised of ribonucleosides. The RNA in a mixture is preferably an mRNA.

As used herein, the term "messenger RNA (mRNA)" refers to a ribonucleic acid that has been transcribed from a DNA sequence by an RNA polymerase enzyme, and interacts with a ribosome to synthesize protein encoded by DNA. Generally, mRNA are classified into two sub-classes: pre-mRNA and mature mRNA. Precursor mRNA (pre-mRNA) is mRNA that has been transcribed by RNA polymerase but has not undergone any post-transcriptional processing (e.g., 5'capping, splicing, editing, and polyadenylation). Mature mRNA has been modified via post-transcriptional processing (e.g., spliced to remove introns and polyadenylated region) and is capable of interacting with ribosomes to perform protein synthesis. mRNA can be isolated from tissues or cells by a variety of methods. For example, a total RNA extraction can be performed on cells or a cell lysate and the resulting extracted total RNA can be purified (e.g., on a column comprising oligo-dT beads) to obtain extracted mRNA.

Alternatively, mRNA can be synthesized in a cell-free environment, for example by in vitro transcription (IVT). IVT is a process that permits template-directed synthesis of ribonucleic acid (RNA) (e.g., messenger RNA (mRNA)). It is based, generally, on the engineering of a template that includes a bacteriophage promoter sequence upstream of the sequence of interest, followed by transcription using a corresponding RNA polymerase. In vitro mRNA transcripts, for example, may be used as therapeutics in vivo to direct ribosomes to express protein therapeutics within targeted tissues.

Traditionally, the basic components of an mRNA molecule include at least a coding region, a 5'UTR, a 3'UTR, a 5' cap and a poly-A tail. IVT mRNA may function as mRNA but are distinguished from wild-type mRNA in their functional and/or structural design features which serve to overcome existing problems of effective polypeptide production using nucleic-acid based therapeutics. For example, IVT mRNA may be structurally modified or chemically modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

A nucleic acid molecule (e.g., DNA or RNA) may comprise naturally occurring nucleotides and/or non-naturally occurring nucleotides such as modified nucleotides. In some embodiments, one or more nucleotides of a polynucleotide includes at least one chemical modification. In some embodiments, a chemical modification is a hydrophobic base modification. Examples of hydrophobic base modifications include but are not limited to 2'OMe modifications, hydrophobic conjugate (e.g., cholesterol) modifications, triazole modifications, etc. In some embodiments, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine. Other exemplary chemical modifications useful in the mRNA described herein include those listed in US Published patent application 2015/0064235.

An "in vitro transcription template (IVT)," as used herein, refers to deoxyribonucleic acid (DNA) suitable for use in an IVT reaction for the production of messenger RNA (mRNA). In some embodiments, an IVT template encodes a 5' untranslated region, contains an open reading frame, and encodes a 3' untranslated region and a polyA tail. The particular nucleotide sequence composition and length of an IVT template will depend on the mRNA of interest encoded by the template.

A "5' untranslated region (UTR)" refers to a region of an mRNA that is directly upstream (i.e., 5') from the start codon (i.e., the first codon of an mRNA transcript translated by a ribosome) that does not encode a protein or peptide.

A "3' untranslated region (UTR)" refers to a region of an mRNA that is directly downstream (i.e., 3') from the stop codon (i.e., the codon of an mRNA transcript that signals a termination of translation) that does not encode a protein or peptide.

An "open reading frame" is a continuous stretch of DNA beginning with a start codon (e.g., methionine (ATG)), and ending with a stop codon (e.g., TAA, TAG or TGA) and encodes a protein or peptide.

As used herein, a "polyadenylated nucleic acid" refers to a nucleic acid molecule having a 3' untranslated region (3' UTR) that comprises a homopolymeric adenosine monophosphate sequence (e.g., comprises multiple, contiguous adenosine monophosphates), also referred to as a "polyA tail". A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates (e.g., any integer between 50 and 250 inclusive). In some embodiments, a polyA tail contains up to 1000 adenosine monophosphates (e.g., any integer between 1 and 1000 inclusive). In a relevant biological setting (e.g., in cells, in vivo, etc.) the poly(A) tail functions to protect mRNA from enzymatic degradation, e.g., in the cytoplasm, and aids in transcription termination, export of the mRNA from the nucleus, and translation.

In some embodiments, a mixture of nucleic acids comprises polyA tail length variants. As used herein, a "tail length variant" refers to a polynucleotide having an identical protein coding sequence to a full-length polynucleotide but having a polyA tail of a different length. For example, if a full length polynucleotide encoding GFP comprises a polyA tail that is 100 nucleotides in length, a GFP tail length variant may have an identical coding sequence but comprise a polyA tail that is 60 nucleotides in length. Generally, tail length variants comprise a polyA tail that is shorter than a full length polynucleotide. In some embodiments, a polyA tail variant has a polyA tail that is between about 1 and about 200 nucleotides (e.g., any integer between 1 and 200) shorter than a wild-type polynucleotide. In some embodiments, a polyA tail variant has a polyA tail that is more than 200 nucleotides shorter than a wild-type polynucleotide.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In some embodiments, an mRNA (e.g., IVT mRNA) is a therapeutic and/or prophylactic mRNA. As used herein, the term "therapeutic mRNA" refers to an mRNA molecule (e.g., an IVT mRNA) that encodes a therapeutic protein. Therapeutic proteins mediate a variety of effects in a host cell or a subject in order to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). As used herein, the term "prophylactic mRNA" refers to an mRNA molecule (e.g., an IVT mRNA) that encodes a prophylactic protein such as a vaccine antigen. Prophylactic proteins mediate a variety of effects in a host cell or a subject in order to prevent disease. Therapeutic and/or prophylactic mRNA may be useful for the treatment of the following diseases and conditions: bacterial infections, viral infections, parasitic infections, cell proliferation disorders, genetic disorders, and autoimmune disorders.

In some aspects, the disclosure provides HPLC methods for separating a nucleic acid from a mixture comprising one or more additional nucleic acids or impurities. A mixture may comprise between about 1 and about 100 nucleic acids. As used herein, the term "impurity" refers to a small molecule, protein, virus, bacterium, etc., that contaminates a composition comprising a desired nucleic acid (e.g., the nucleic acid sought to be separated from the mixture). In some embodiments, an impurity is a degradation product. As used herein, "degradation product" refers to a nucleic acid fragment that is a product of the degradation (e.g., enzymatic degradation) of a polyadenylated nucleic acid. For example, in some embodiments, a degradation product is a tail variant of an mRNA.

A nucleic acid may be larger or smaller than the one or more other nucleic acids or impurities in a mixture. For example, a larger nucleic acid may comprise about 10-100%, 25-100%, 50-100%, 50-75%, 100-200%, 200-500% or 500-1000% more nucleotides than the one or more additional nucleic acids or impurities in a mixture. Alternatively, a smaller nucleic acid may comprise about 10-100%, 25-100%, 50-100%, 50-75%, 100-200%, 200-500% or 500-1000% fewer nucleotides than the one or more additional nucleic acids or impurities in a mixture. In some embodiments, an impurity is a degradation product, for example a fragment (e.g., polynucleotide) that has been cleaved from a nucleic acid (e.g., an mRNA).

In some embodiments, HPLC methods as described by the disclosure are capable of separating nucleic acids with tail lengths that are closely related in size (e.g., mRNAs having identical coding sequence lengths but differing in polyA tail length or in number of hydrophobic modifications). For example, in some embodiments, HPLC methods as described by the disclosure separate nucleic acids having a difference in polyA tail length of between about 1 and about 100 adenosine monophosphates (e.g., any integer between 1 and 100, inclusive, e.g., 1, 2, 3, 4, 5, 10, 15, 20, 25, 30, 40, 50, 60, 75, 90, 95, 99, or 100). In some embodiments, HPLC methods as described by the disclosure separate nucleic acids having a difference in the number of hydrophobic modifications of between about 1 and about 100 modifications (e.g., any integer between 1 and 100, inclusive, e.g., 1, 2, 3, 4, 5, 10, 15, 20, 25, 30, 40, 50, 60, 75, 90, 95, 99, or 100).

Delivery of mRNA molecules to a subject in a therapeutic context is promising because it enables intracellular translation of the mRNA and production of at least one encoded peptide or polypeptide of interest without the need for nucleic acid-based delivery systems (e.g., viral vectors and DNA-based plasmids). Therapeutic mRNA molecules are generally synthesized in a laboratory (e.g., by in vitro transcription). However, there is a potential risk of carrying over impurities or contaminants, such as incorrectly synthesized mRNA and/or undesirable synthesis reagents, into the final therapeutic preparation during the production process. In order to prevent the administration of impure or contaminated mRNA, the mRNA molecules can be subject to a quality control (QC) procedure (e.g., validated or identified) prior to use. Validation confirms that the correct mRNA molecule has been synthesized and is pure.

Certain aspects of the disclosure relate to the discovery that HPLC methods described herein are useful, in some embodiments, for quality control of certain nucleic acid molecules (e.g., polyadenylated nucleic acids, such as mRNA).

Accordingly, in some aspects the disclosure provides a method of quality control of a pharmaceutical composition comprising a nucleic acid having a hydrophobic portion (e.g., a polyadenylated nucleic acid, such as intact mRNA), the method comprising: separating the nucleic acid from a mixture comprising one or more additional nucleic acids or impurities by a HPLC method as described herein; comparing the separated nucleic acid with a reference nucleic acid; and determining the polyadenylated nucleic acid has a desired hydrophobic character (e.g., has a full length polyA tail or comprises a desired hydrophobic base modification) based on a comparison of the separated nucleic acid with the reference nucleic acid.

In some embodiments, the determining step further comprises quantifying an amount of nucleic acid having a reduced hydrophobic character in the pharmaceutical composition (e.g., polyadenylated nucleic acids having no or shortened polyA tails). Without wishing to be bound by any particular theory, the ratio of tailless nucleic acid to tailed nucleic acid in a mixture is indicative of the stability, and thus potency, of the nucleic acid in pharmaceutical composition.

In some instances, the methods of the disclosure are used to determine the purity of an RNA sample. The term "pure" as used herein refers to material that has only the target nucleic acid active agents such that the presence of unrelated nucleic acids is reduced or eliminated, i.e., impurities or contaminants, including RNA fragments (e.g., tail variants and/or other degradation products). For example, a purified RNA sample includes one or more target or test nucleic acids but is preferably substantially free of other nucleic acids. As used herein, the term "substantially free" is used operationally, in the context of analytical testing of the material. Preferably, purified material substantially free of impurities or contaminants is at least 95% pure; more preferably, at least 98% pure, and more preferably still at least 99% pure. In some embodiments a pure RNA sample is comprised of 100% of the target or test RNAs and includes no other RNA. In some embodiments it only includes a single type of target or test RNA.

A "reference nucleic acid" as used herein refers to a control nucleic acid (e.g. a nucleic acid having a hydrophobic portion, such as intact mRNA) or chromatogram generated from a control nucleic acid that uniquely identifies a polyadenylated nucleic acid separated from a mixture. The reference nucleic acid may be generated based on digestion of a pure sample and compared to data generated by HPLC of a mixture comprising the nucleic acid of interest. Alternatively it may be a known chromatogram, stored in a electronic or non-electronic data medium. For example, a control chromatogram may be a chromatogram based on predicted HPLC retention times of a particular RNA (e.g., a test mRNA). In some embodiments quality control methods described by the disclosure further comprise the step of comparing the nucleic acid separated from the mixture to the reference nucleic acid using an orthogonal analytical technique, for example polymerase chain reaction (e.g., RT-qPCR), nucleic acid sequencing, gel electrophoresis, mass spectrometry, etc.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

EXAMPLES

Example 1: Reversed Phase HPLC Methods for the Determination of mRNA polyA Tail Content Examples of a first HPLC method and a second HPLC method are shown below in Table 1.

TABLE 1

| HPLC Methods | | |
|---|---|---|
| | First Generation | Second Generation |
| Mobile Phase System | 100 mM triethylammonium acetate (TEAA)/100 mM ammonium phosphate pH 7.0-7.05 | 100 mM tris acetate (Tris) 2.5 mM EDTA pH 7.0 ± 0.1 |
| Organic Eluent | 10% hexylene glycol 25% acetonitrile | 25% acetonitrile |
| Column | Agilent PLRP-S 8 µm, 4000 A 150 × 2.1 mm | Thermo DNApac RP 4 µm, 1000-2000 A 100 × 2.1 mm |
| Temperature | 80° C. | 80° C. |
| Run Time | 36 minutes | 15 minutes |

Both generations of the HPLC tail method are able to separate intact mRNA by polyA tail length, with baseline resolution between the tailless and full-length tail populations. As shown in FIG. 1, the loss mass associated with a full-length polyA tail with heat stress correlates with the drop in mRNA expression in HeLa cells. Both methods show a similar rate of formation of tailless species.

Several undesirable characteristics have been observed in the first generation HPLC tail assay described above, including:
1. low signal, indicating low off-column recoveries;
2. short column lifetime of approximately 100 injections, including extensive conditioning requirements;
3. variability in column performance, both between and within column lots;
4. inconsistent peak shape of several mRNA samples measured;
5. excessive in-run degradation increasing with overall mRNA length, leading to overestimation of the tailless population;
6. unstable, pH-sensitive mobile phases.

The second generation tail assay described by the disclosure has addressed many of these issues with full characterization of selectivity, robustness, reproducibility, and mRNA stability. A range of tail standards and prophylactic mRNA samples were used to assess the quality and robustness of the second-generation HPLC tail method, and are listed in Table 2 below.

TABLE 2

| mRNA samples | | |
|---|---|---|
| mRNA Name | Theoretical Length | polyA Tail |
| Standard 1 | 851 (A100) | 0, 40, 100 |
| Standard 2 | 1922 (A100) | 0, 40, 100 |
| Standard 3 | 4016 (A100) | 40, 100 |
| mRNA 1 | 1952 | 100 |
| mRNA 2 | 1955 | 100 |
| mRNA 3 | 845 | 100 |

TABLE 2-continued mRNA samples

| mRNA Name | Theoretical Length | polyA Tail |
|---|---|---|
| mRNA 4 | 1448 | 100 |
| mRNA 5 | 4016 | 100 |
| mRNA 6 | 843 | 100 |
| mRNA 7 | 1929 | 100 |
| mRNA 8 | 1871 | 100 |
| mRNA 9 | 2341 | 100 |
| Tailless mRNA 9 | 2241 | 0 |
| mRNA 10 | 1927 | 100 |
| mRNA 11 | 1994 | 100 |

Embodiments of HPLC method parameters are listed in Tables 3 and 4 below.

TABLE 3

HPLC operating parameters

| | |
|---|---|
| Instrument | Agilent 1260/1290 or equivalent |
| Column | Thermo DNApac RP, PN 088923 |
| Mobile Phase A | 100 mM Tris Acetate/2.5 mM EDTA pH 7.0 ± 0.1 |
| Mobile Phase B | 25% acetonitrile, 100 mM Tris Acetate/2.5 mM EDTA pH 7.0 ± 0.1 |
| Run time | 15 minutes |
| Detection | UV at 260 nm; 10 Hz data rate |
| Injection volume | 5-25 µL |
| Column temperature | 80° C. |
| Autosampler temperature | 5° C. |
| Sample concentration | 0.1 mg/mL |
| Sample diluent | Water |

TABLE 4

HPLC Gradient Parameters

| Time (min) | % MPA | % MPB | Flow (mL/min) |
|---|---|---|---|
| 0 | 100 | 0 | 0.2 |
| 1 | 100 | 0 | 0.2 |
| 1.5 | 100 | 0 | 0.25 |
| 2 | 94 | 6 | 0.35 |
| 6 | 76.5 | 23.5 | 0.4 |
| 7 | 0 | 100 | 0.4 |
| 9 | 0 | 100 | 0.4 |
| 9.1 | 100 | 0 | 0.4 |
| 15 | 100 | 0 | 0.4 |

The mobile phases used for initial method development at pH 8.1-8.5 were prepared from Sigma 50×TAE (part no. SRE0033-1L, 2M Tris and 50 mM EDTA). For all development at pH 7.0 and pH screening, stock 400 mM Tris Acetate/10 mM EDTA was prepared in-house as follows:
1. Weigh 48.46 g of tris base into a clean 1 L bottle.
2. Add 950 mL of MilliQ water. Mix well to dissolve.
3. Add 20 mL of 0.5 M EDTA solution. Mix well.
4. Titrate with acetic acid to desired pH.
5. Fill to 1 L with MilliQ water. Filter through a 2 µm filter.

In some embodiments, Corning 10×TAE (Ref #46-010-CM, 400 mM Tris/10 mM EDTA) was shown to be equivalent to the in-house preparation. The 10× stock is titrated with concentrated acetic acid (approximately 6-8 mL to bring 1 liter from the initial pH 8.4 to 7.0). Given the small volume of acid required, no adjustment is made for tris concentration, although actual mobile phase concentration after pH adjustment drops to approximately 99 mM tris due to the dilution.

The dominant selectivity by tail can be attributed to the intrinsic hydrophobicity of adenosine compared to the other nucleobases. The long stretch of adenosines at the 3' end acts as a hydrophobic tag, increasing retention in a reversed phase system. The tris counterion contributes very little to the overall hydrophobicity of the molecule compared to more traditional hydrophobic alkyl chain ion pairs, so the separation is almost exclusively dependent on the tail length. The poly-styrene divinylbenzene (PS-DVB) stationary phase was designed with a distribution of pores between 1000 and 2000 Å, allowing diffusion and full access of large biomolecules like mRNA to the hydrophobic surface area without exclusion-based effects on the chromatography.

Figure 2:
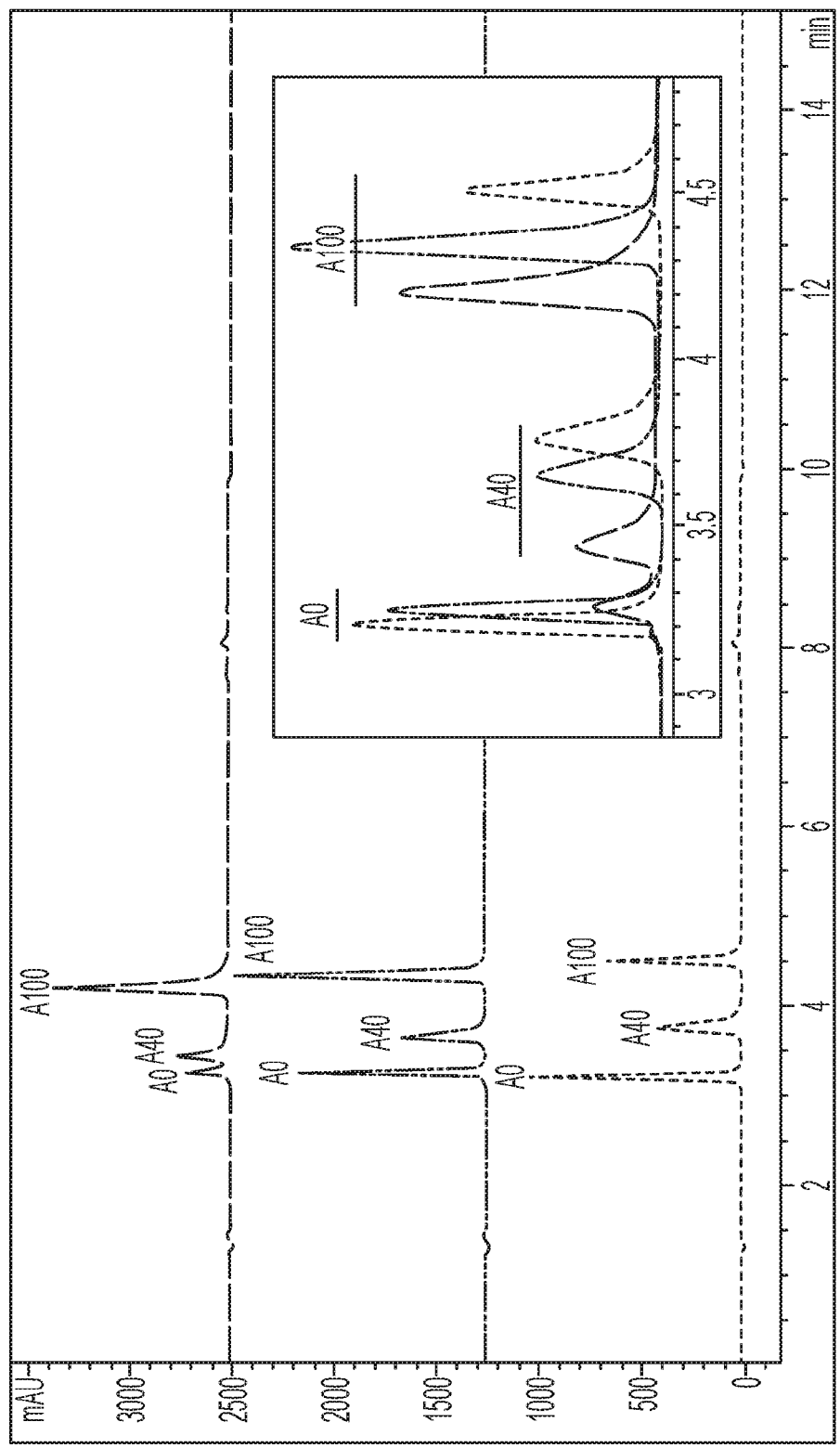
FIG. 2 shows a representative histogram for separation of A0, A40, and A105 tail Standard 3 (top), Standard 2 (middle), and Standard 1 (bottom). Baseline resolution of tailless, polyA100, and polyA40 is preserved independent of overall length. As shown in the overlay (inset), retention of the tailless material increases slightly with length of the entire RNA molecule, but the opposite is true of the polyadenylated species.

The selectivity and resolution was demonstrated with mRNA tail length variants of three different overall lengths; in FIG. 2, mixtures of tailless, A40, and A105 standards of Sample 3 (A100: 851 nt), Sample 2 (A100: 1922), and Sample 1 (A100: 4016) are separated with baseline resolution. Although tail length dominates the separation, absolute retention time varies between the different mRNA molecules; in general, retention of mRNA of a fixed tail length decreases as the total length increases, as the mixed-base, less hydrophobic sequence increases in proportion to the tail. The opposite tends to be true for tailless species, without the polyA skewing retention, longer sequences have more available sites for interaction with the stationary phase (FIG. 2, inset).

Analytical mass balance was demonstrated by comparing the total peak area of an analytical run to the same injection through a union, where the material bypasses the column. Near-quantitative recoveries were observed, independent of the length of the sequence (Table 5).

TABLE 5

Mass recovery. The total chromatogram peak area of mRNA samples was compared to the area of an injection of the same sample bypassing the column.

| mRNA | Length | Mass Balance |
|---|---|---|
| mRNA 3 | 845 | 105% |
| mRNA 2 | 1955 | 97% |
| mRNA 9 | 2341 | 103% |

Figure 3:
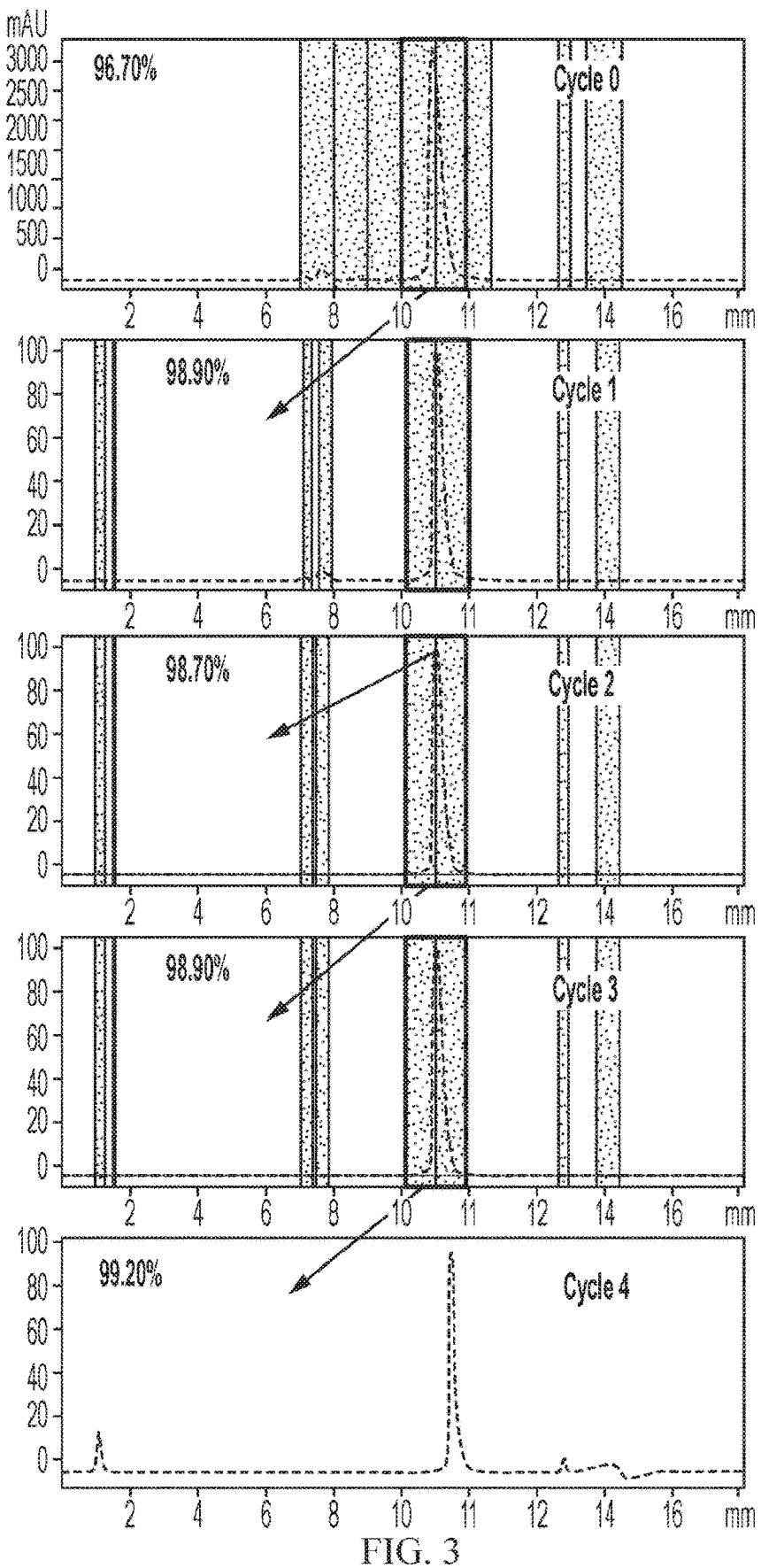
FIG. 3 shows representative data for evaluation of in-run degradation of mRNA 3. Iterative reinjection of the main peak revealed consistent 1% observed degradation.

To assess total in-run degradation, the main peak of mRNA 3 was iteratively collected and reinjected for four cycles (FIG. 3). Integration of each resulting chromatogram revealed a constant tailless population of approximately 1% generated by each collection and reanalysis. When a single cycle of this experiment was repeated with longer constructs such as mRNA 9 and mRNA 5, the most degradation observed was 3%.

Figure 4:
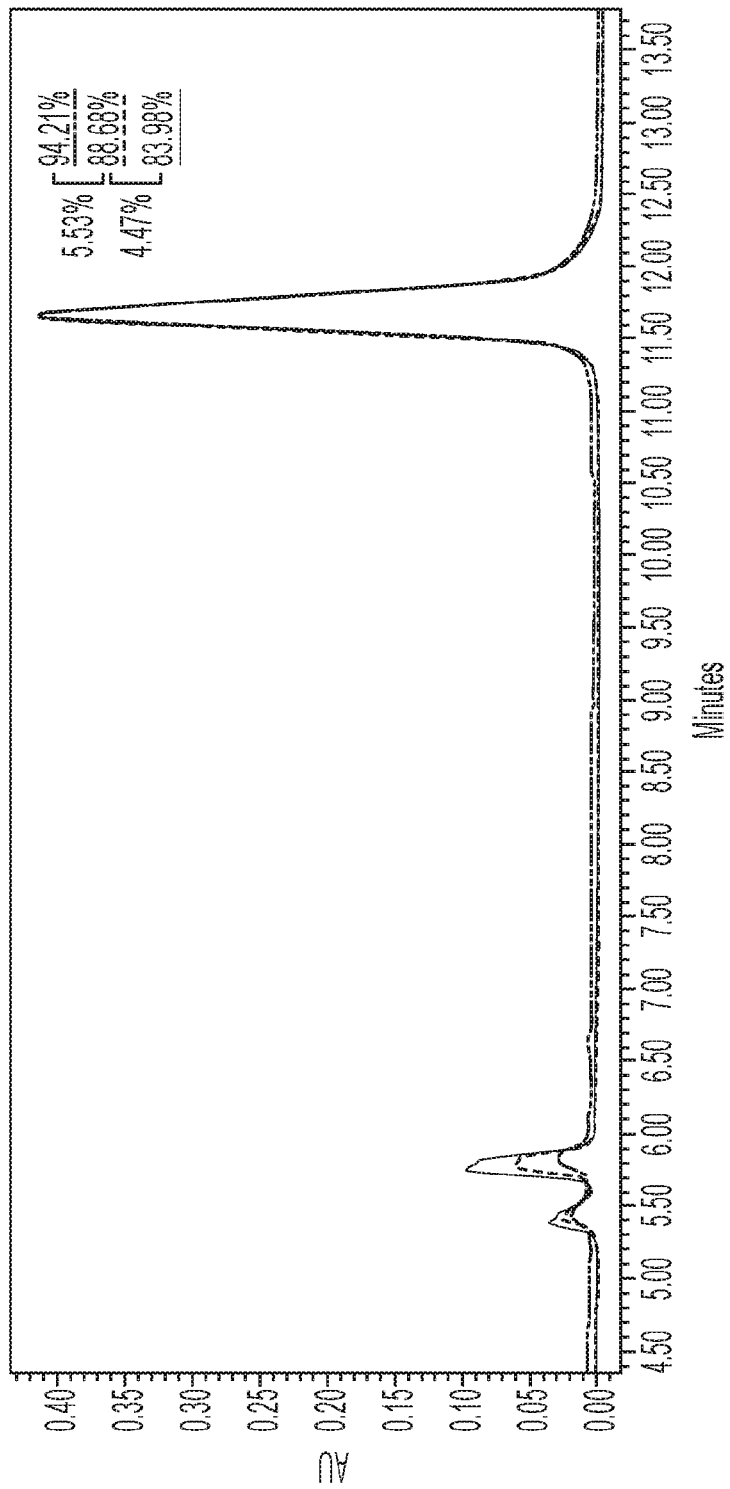
FIG. 4 shows representative data for spike and recovery of tailless mRNA 3 (collected) in full-length mRNA 3. Overlaid are initial mRNA 3, a tailless spike at 5%, and a tailless spike at 10%. The % tailed by integration is shown at the top right; the additional 5% tailless spike is observed in each sample.
Figure 5:
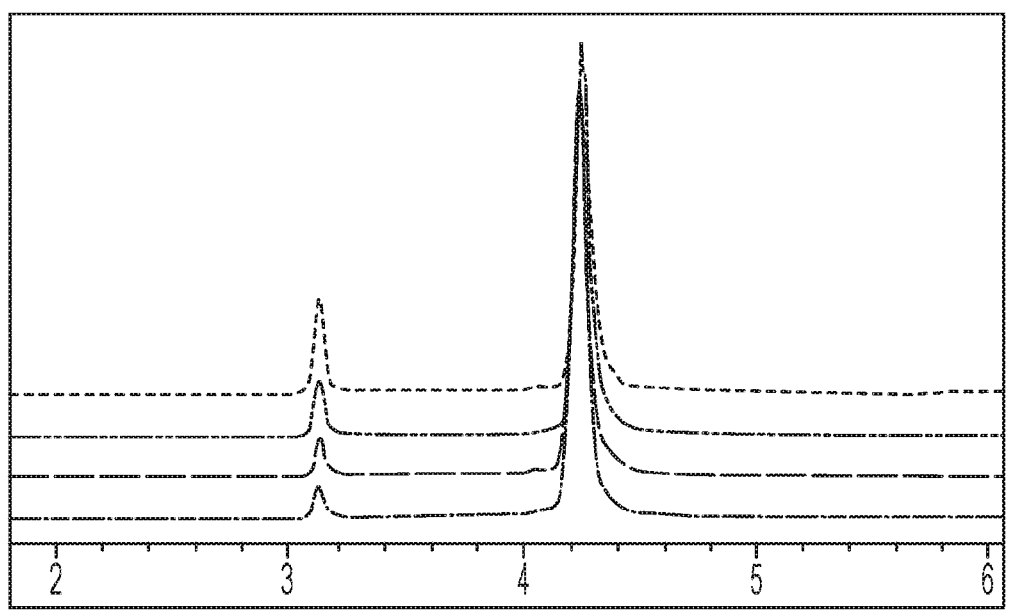
FIG. 5 shows representative data for spike and recovery of the tailless mRNA 9 in standard mRNA 9. The corresponding chromatograms are stacked, where the increase in the tailless peak from 1% spike (bottom) to 10% spike (top) is clear.

Selective recovery of tailed vs. tailless RNA populations was probed through multiple spike-and-recovery experiments and iterative collection and analyses. In the first, the tailless peak was collected from several analytical injections of mRNA 3, concentrated, and spiked back into the initial sample at 5% and 10%. When each chromatogram was integrated, the expected 5% and 10% increase in the tailless peak was observed (FIG. 4). To demonstrate the same mass balance for a longer mRNA, tailless mRNA 9 was spiked into full length-mRNA 9 at levels from 1% to 10%, and in each case there was an increase in tailless material detected (Table 6 and FIG. 5).

TABLE 6

Spike and recovery of the tailless mRNA 9 in standard mRNA 9. The corresponding chromatograms are stacked in FIG. 5, where the increase in the tailless peak from 1% spike (bottom) to 10% spike (top) is clear.

| Sample | % Tailed | Change in % tailless | % Accuracy |
|---|---|---|---|
| mRNA 9 (initial) | 94.8 | — | — |
| mRNA 9 + 1% TL | 93.9 | 0.9% | 90% |
| mRNA 9 + 2% TL | 93.0 | 1.8% | 90% |
| mRNA 9 + 5% TL | 90.6 | 4.2% | 84% |
| mRNA 9 + 10% TL | 85.5 | 9.3% | 93% |

Method performance was shown to be significantly impacted by mobile phase pH, column temperature, tris concentration, and column residence time. Each was individually evaluated for impact on mRNA stability and chromatographic performance across the development candidates to select final method conditions.

Figure 6:
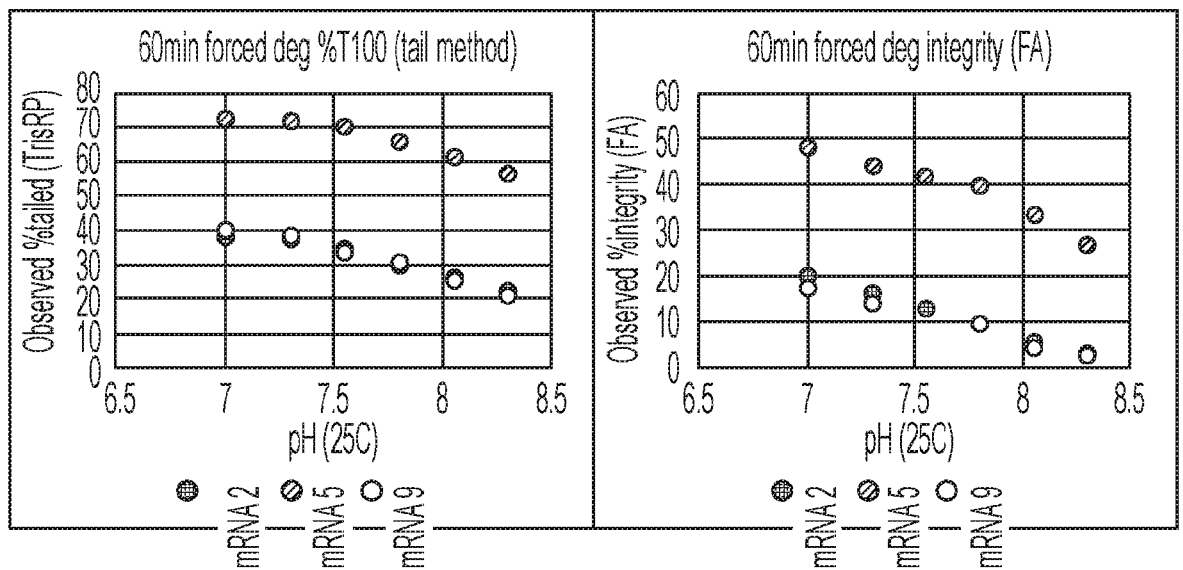
FIG. 6 shows representative data for in-solution degradation in TAE pH7.0-8.3. mRNA integrity was assessed by the second generation HPLC tail method (left) and Fragment Analyzer Capillary Electrophoresis (FA-CE) (right). Less degradation was apparent by both measurements at lower pH.

Mobile phase pH was assessed from 8.3, the typical pH of TAE for biological applications, down to pH 7.0. The effect on mRNA stability was assessed by an in-solution forced degradation study, quantified by both the second generation HPLC methods described herein and Fragment Analyzer Capillary Electrophoresis (FA-CE) (FIG. 6). Stock TAE (400 mM tris/10 mM EDTA) was prepared between pH 7.0 and 8.3 by titrating tris base and EDTA with acetic acid, as described herein. Samples of mRNA 2, mRNA 3, and mRNA 9 were then diluted to 200 mM TAE with the prepared buffers and heated to 80° C. in solution for 1 hour.

Figure 7:
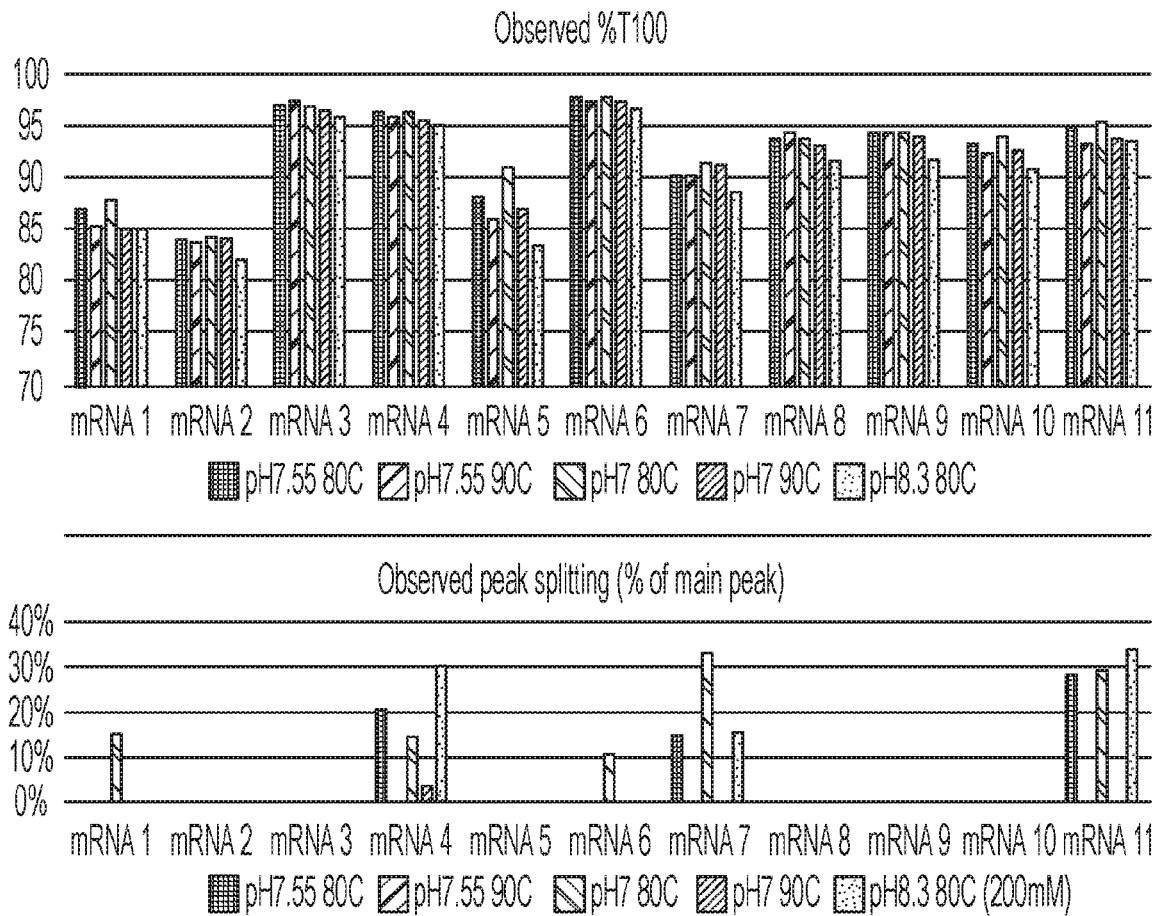
FIG. 7 shows representative data from a temperature, pH, and mobile phase concentration combined study. To assess the impact of the mobile phase and temperature optimization, 100 mM TAE mobile phases were run at 80° C. and 90° C., and the resulting % tailed and extent of peak splitting compared to the initial method conditions (200 mM tris at pH 8, 80° C.). A 20-minute, high resolution gradient method was used for all analyses. All four conditions resulted in substantially reduced in-run degradation. At both pH 7.0 and pH 7.55, 80° C. was insufficient to eliminate split peaks for the gradient used, but all were eliminated at 90° C. Among the four optimized conditions tested, the lower pH and lower temperature resulted in slightly less degradation by a margin of between 0.4% and 2.5% for all samples tested with the exception of mRNA 5, the longest and least stable, with a range of 5%, which was most damaged by increasing the temperature to 90° C.

Both measurements revealed a slower rate of in-solution degradation as the pH approached 7.0, resulting in improved mRNA stability in the lower range of the tris buffer. This study is not meant to be predictive of a rate of in-run degradation, as some stability is conferred while RNA is adsorbed to the column, but rather to map mRNA stability at high temperatures in the mobile phase of interest. Reducing the mobile phase pH in turn reduced the in-run degradation, resulting in higher observed % tailed populations (see pH 7.0 vs. 7.55 in FIG. 7). Increased retention at lower pH allows lower overall mobile phase concentrations without sacrificing robust retention of the tailless peak, which has a number of benefits on both the chromatography and the instrument.

It is important to note that all pHs indicated here refer to the measurement at room temperature, between 20 and 25° C. Tris pH drops with temperature, resulting in a much lower effective pH at elevated temperatures. Based on this assessment, the method pH was fixed at 7.0.

Figure 8:
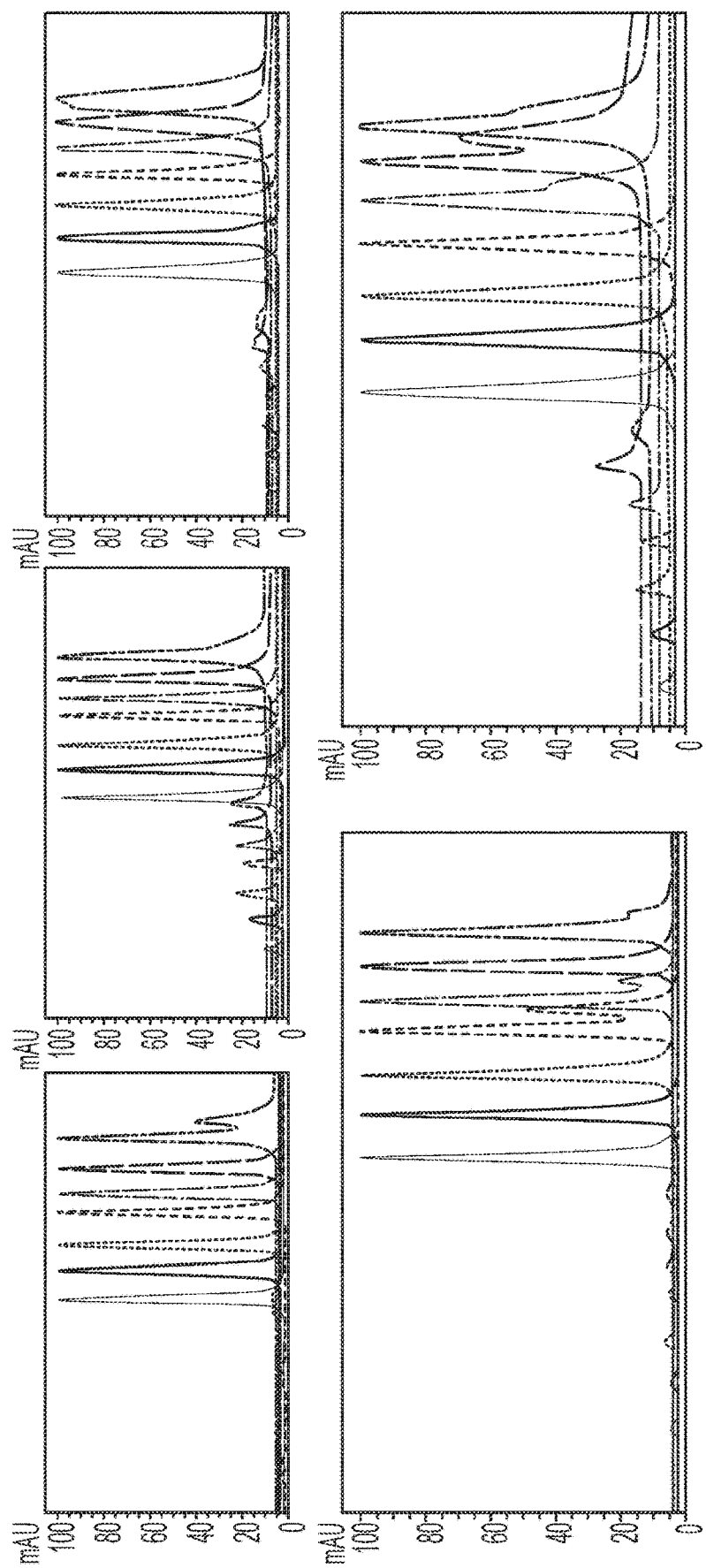
FIG. 8 shows representative data for the effect of run temperature on peak shape. Elution regions are overlaid of (clockwise from top left) mRNA 3, mRNA 2, mRNA 9, mRNA 7, and mRNA 4 analyzed at 70° C., 75° C., 80° C., 85° C., 90° C., 95° C., and 100° C. The gradient is unchanged; the peak shifts to the left as temperature is increased. mRNA 4 and mRNA 7 experience a significantly higher "melting point" than the other three.

Although high temperature accelerates mRNA degradation, it is frequently used to provide sufficiently denaturing chromatographic conditions to eliminate effects of mRNA structure or multimeric states on peak shape. Peak splitting, in which the tail end of the main peak exhibits a shoulder or secondary peak, was routinely observed in early versions of this method for a problematic subset of samples tested, primarily mRNA 4, mRNA 7, mRNA 11, and mRNA 10. Temperature studies between 70° C. and 100° C. including both the problematic mRNAs and those not exhibiting this phenomenon revealed the impact of temperature. At 70° C., all mRNAs tested exhibited some degree of a back shoulder, which disappeared at different temperatures for different molecules, indicating a unique transition temperature for each molecule to sufficiently denature (FIG. 8).

Figure 9:
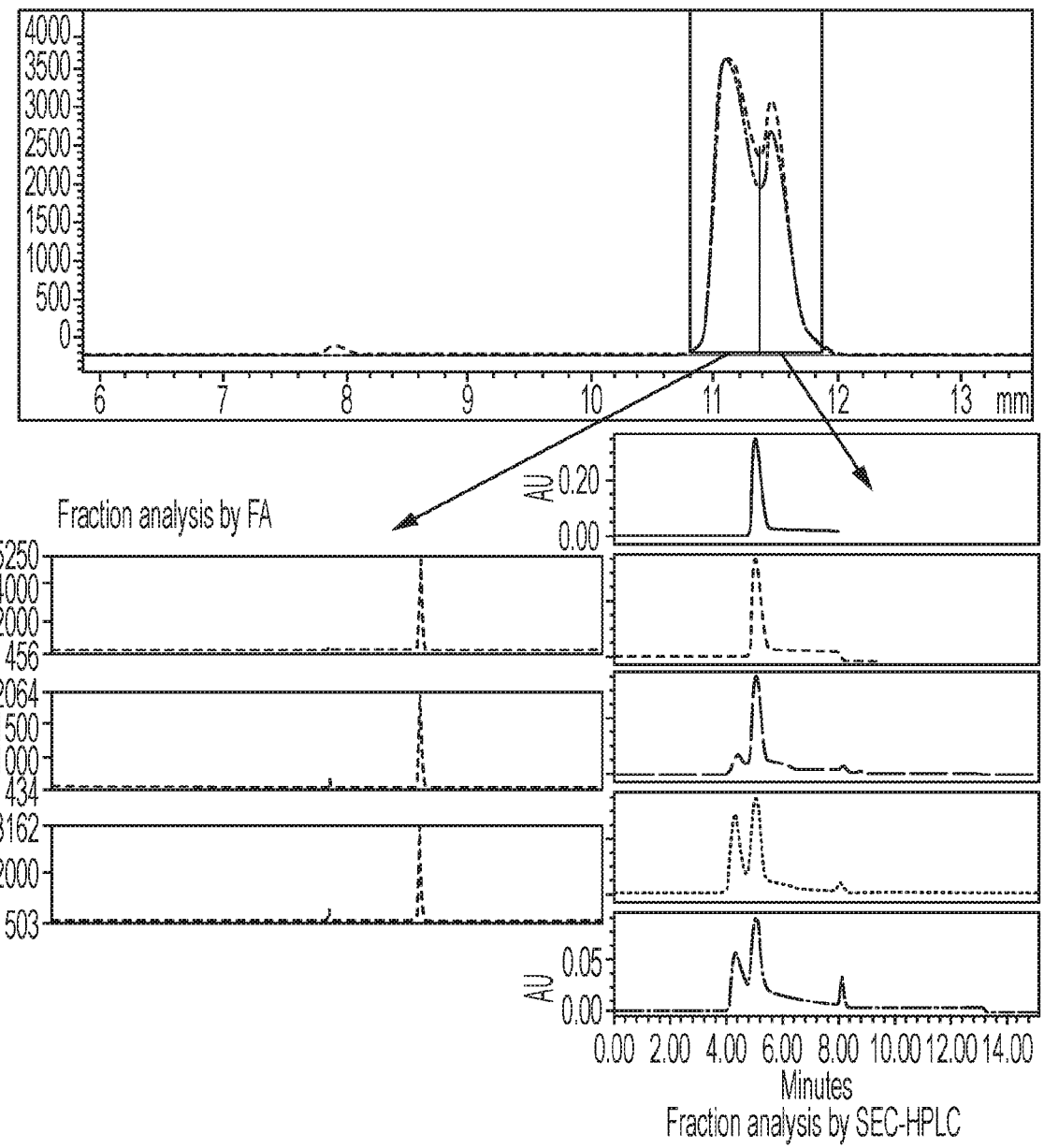
FIG. 9 shows representative data for the investigation into the split peak of mRNA 4. Five fractions were collected across the split tailed peak of mRNA 4, and analyzed by both FA-CE (left) and non-denaturing size-exclusion chromatography HPLC (SEC-HPLC) (right). The earlier eluting SEC peak in the later fractions indicates a larger species, which may be higher order mRNA structure. FA-CE indicates that the same species are present.

The cause of the low-temperature peak splitting was investigated by isolating the regions of the split peak of a large analytical injection of mRNA 4 (FIG. 9, top). Analysis of both regions of the peak by FA-CE revealed no detectable difference in mRNA size distribution, but non-denaturing size exclusion chromatography (SEC) revealed a second discrete species emerging in the back shoulder. SEC HPLC run parameters are shown in Table 7. The earlier retention time in SEC indicates a much larger species, and that, in conjunction with the FA-CE data and temperature dependence, supports a stabilized structural conformer or transient multimer separated in the tail method chromatography that is sufficiently denatured by the FA-CE run conditions (FIG. 9).

TABLE 7

SEC-HPLC run parameters

| | |
|---|---|
| System | Waters H-Class UPLC |
| Mobile Phase | 100 mM Tris Acetate/2.5 mM EDTA pH 8.3 |
| Column | Waters BEH 2.5 μm 450 A 150 × 4.6 mm (PN 186006852) |
| Column temperature | 25° C. |
| Flow rate | 0.25 mL/min |
| Injection volume | 10 μL |
| Sample concentration | 100 ng/μL |

Figure 10:
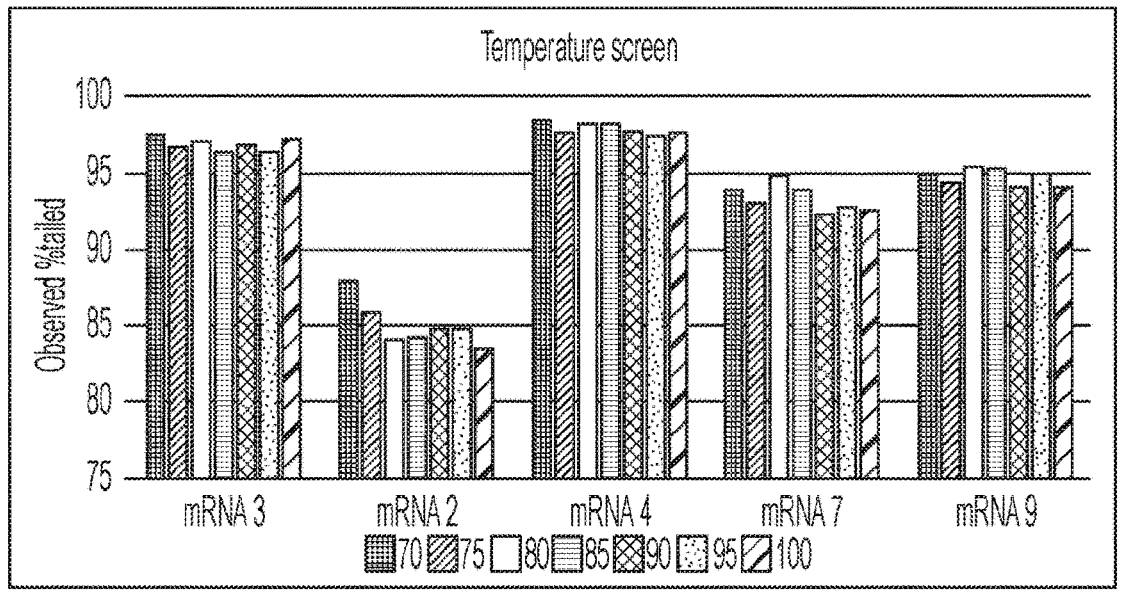

Since high temperature proved effective at eliminating the split peaks in all constructs, the impact on in-run degradation was evaluated to confirm the feasibility of a 90° C. method. Although there was some loss in % tailed observed at higher temperature (FIG. 10), differences were generally within 3% for each mRNA. Moving forward as available HPLC instrumentation allows, an increase of the run temperature to 85° C. or 90° C. for molecules that exhibit a split peak that is not resolved by the mobile phase and residence time optimization will be used.

Figure 11:
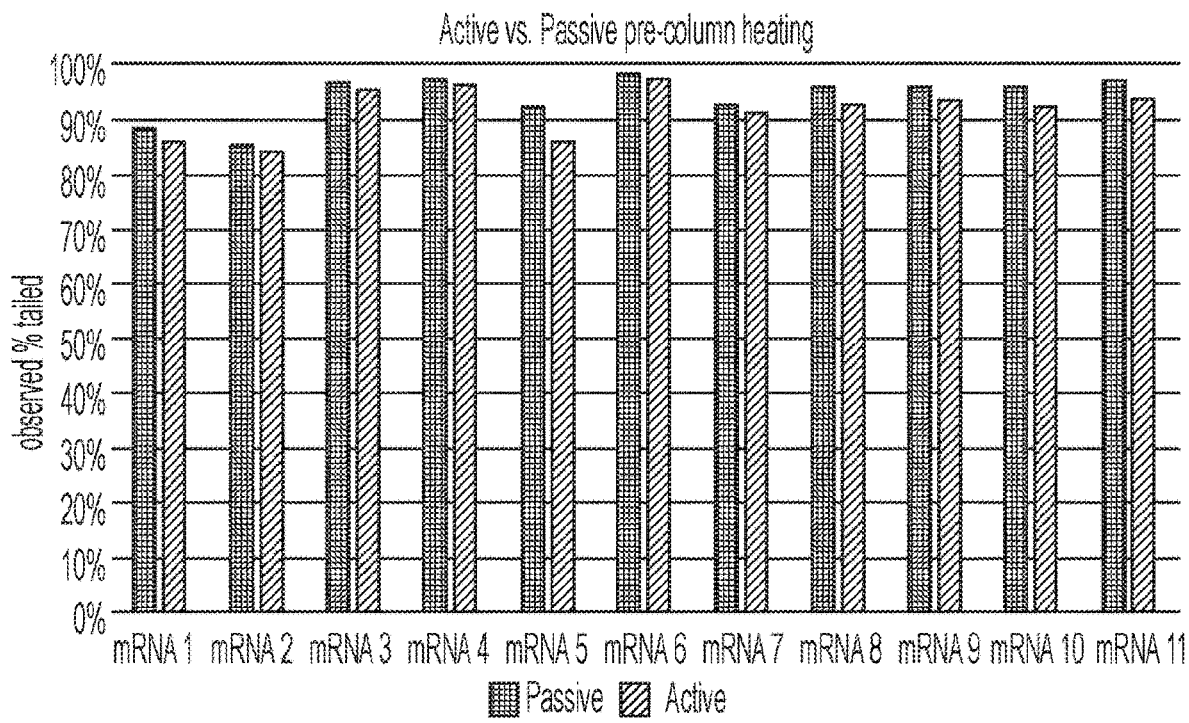
FIG. 11 shows representative data for a Mode of pre-column heating. Use of the active solvent preheater at 80° C. on the Waters H-Class gave significantly lower reported % tailed than the passive heat exchanger on an Agilent 1290 HPLC.

The mode of pre-column heating affects the chromatography as well. In some embodiments, HPLC methods described herein are performed with a heat exchanger that reaches the temperature of the column oven to heat the mobile phase pre-column, or "passive preheating". "Active preheating", a feature on both Waters and Thermo UPLC platforms, resulted in increased in-run degradation for all molecules tested (FIG. 11), although peak splitting was largely eliminated. The difference in observed % tailed between the two modes was most apparent at 7% for mRNA 5; for all other samples tested, differences were 1% to 4%.

Figure 12:
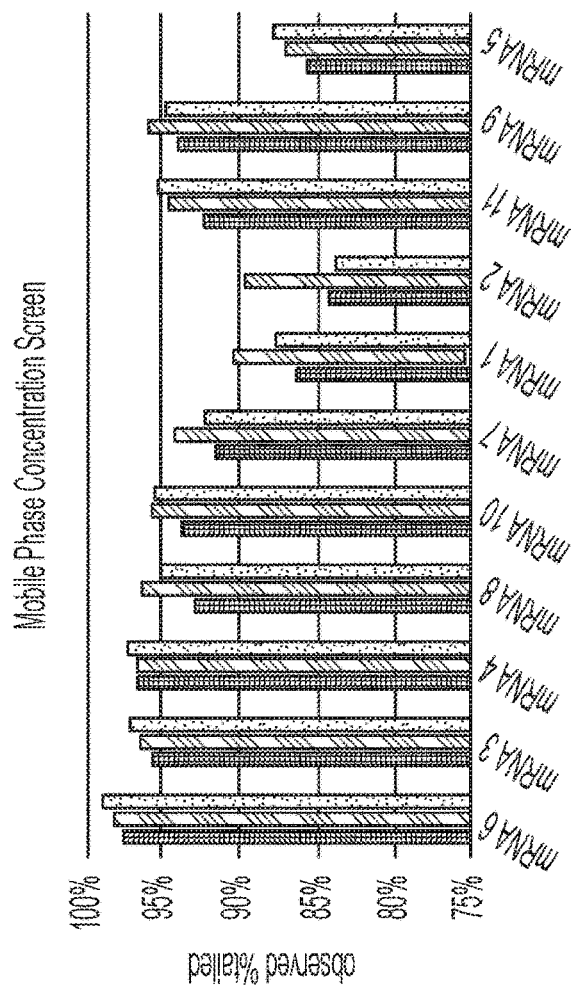
FIG. 12 shows representative data for the effect of mobile phase concentration on observed % T100 at pH 7. Observed % tailed generally increases as the mobile phase concentration is lowered from 200 mM to 100 mM. Low pH is required for robust binding at the 100 mM condition.

Mobile phase concentration was selected for robust retention, peak shape, and mRNA stability. Higher mobile phase concentrations can contribute to both increased in-run degradation (FIG. 12) and increased peak splitting.

Figure 13:
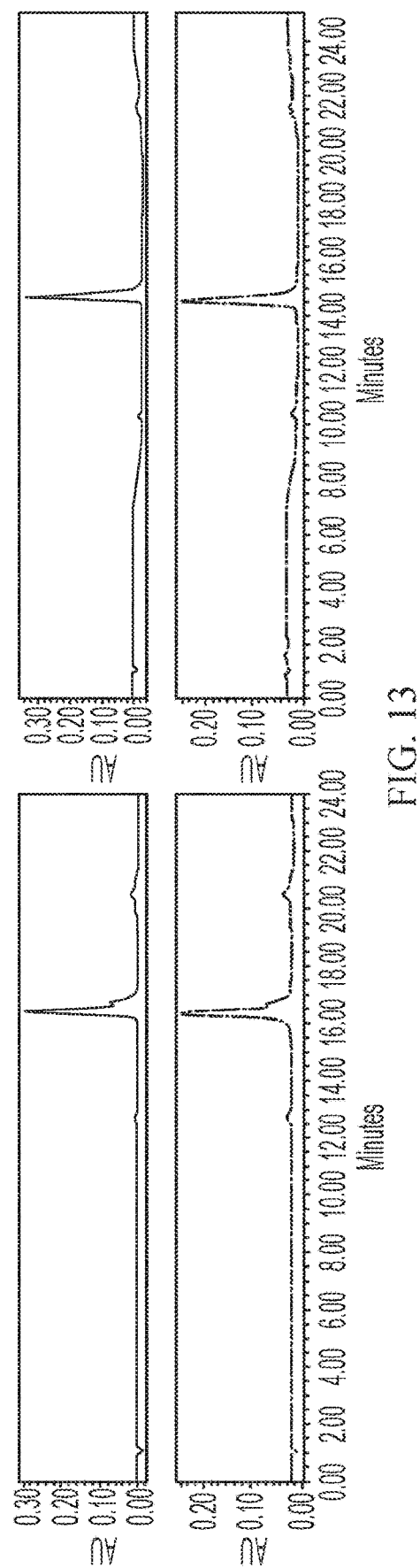
FIG. 13 shows representative data for eliminating peak splitting through mobile phase concentration. mRNA 4 (top) and mRNA 7 (bottom) consistently exhibit a back shoulder at 100 mM TAE pH 7, 80° C. with passive preheating (left). At right, the mobile phase concentration is stepped down to 20 mM for the gradient, eliminating the split peak. The baseline drops slightly with the lower mobile phase concentration.

Further reducing the mobile phase concentration revealed the role of the buffer in creating or stabilizing the split peaks. On a quaternary HPLC system, initial conditions of 100 mM tris were used for robust binding, then stepped down to 20 mM for the elution gradient (FIG. 13). All peak splitting observed at the constant 100 mM conditions were eliminated at the low mobile phase concentration, while resolution between tail and tailless is preserved. Although it requires additional solvent blending capabilities, this observation provides another approach to eliminating split peaks.

The gradient and flow rate were optimized to minimize mRNA residence time on the column and reduce time of analysis (see Table 4). The 0.2 mL/min flow rate at the beginning of the method allows robust binding, but is quickly stepped up for the gradient to preserve resolution in a short run time. Extensive re-equilibration returns the column to aqueous conditions on the back end of the method, as very low levels of organic prevent sample binding.

Figure 14:
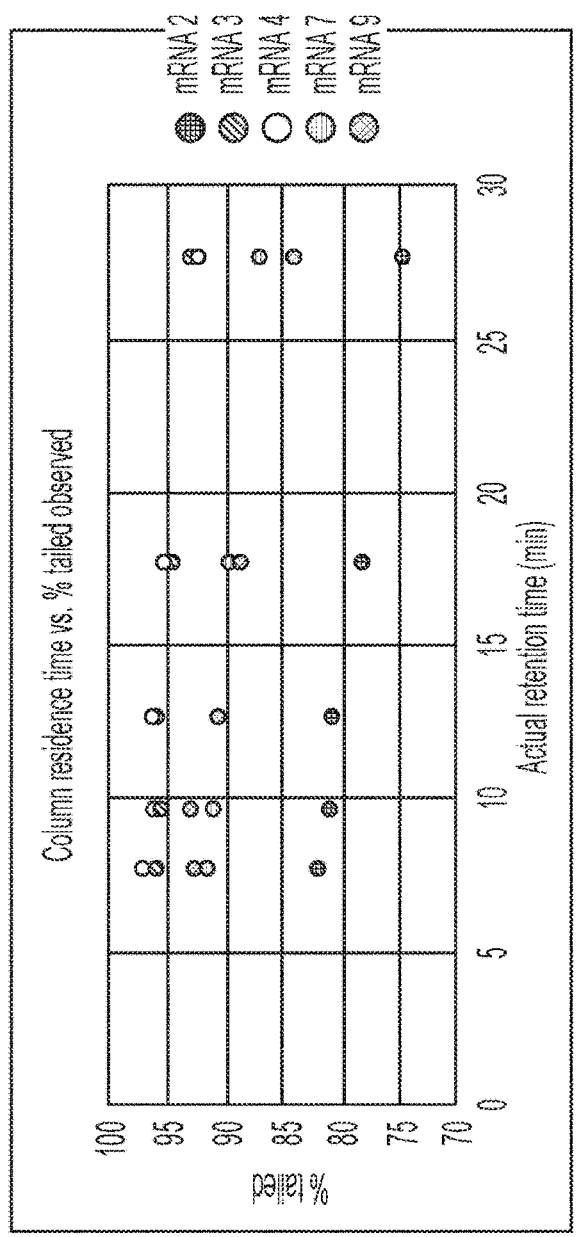
FIG. 14 shows representative data for the effect of residence time on reported % tailed. Retention time was increased by adding a hold time at initial conditions (100% aqueous) before the gradient.
Figure 15:
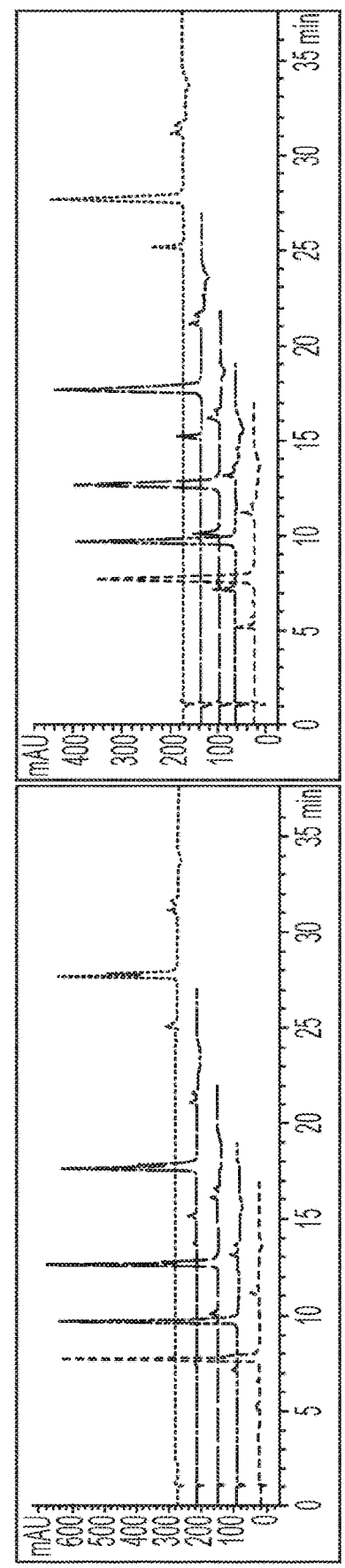
FIG. 15 shows representative data for the effect of residence time on peak splitting. The area under the back peak of mRNA 4 (left) and mRNA 7 (right) increases as the retention time is increased with an initial hold time.

To assess the impact of residence time, hold times were introduced at the beginning of the method, where the mRNA remains bound before the gradient. For each of the five constructs tested, the measured tailless population increased, indicating degradation occurring while the mRNA is bound to the column (FIG. 14). Peak splitting also becomes more prevalent with a longer residence time (FIG. 15). The shortened run time significantly improves both issues, in addition to the benefit of higher throughput. In conjunction with the other method parameters, shortened residence time and an accelerated gradient sufficiently minimized peak splitting for consistent main peak morphology of all molecules tested.

All samples used for method optimization were final purified material, in the range of 1-2 mg/mL in 2 mM sodium citrate. These were then diluted to 100 ng/µL in water for analysis. Because of the weak retention of the Tris mobile phase system, any additional components in the sample milieu can impact adsorption or retention. Counterions associated with the mRNA can act as additional ion pair, increasing the retention. This is most notable for residual alkylammonium ions, such as TEAA, left over from reversed phase purifications, although any salt at a sufficiently high concentration can have the same effect. Conversely, it takes very little organic content to prevent binding to the column; residual solvents used in-process such as hexylene glycol, ethanol, or acetonitrile can cause column breakthrough. When testing in-process samples, where sample diluent may be more variable, it is therefore important to fully buffer exchange into water to obtain a reproducible retention time.

Figure 16:
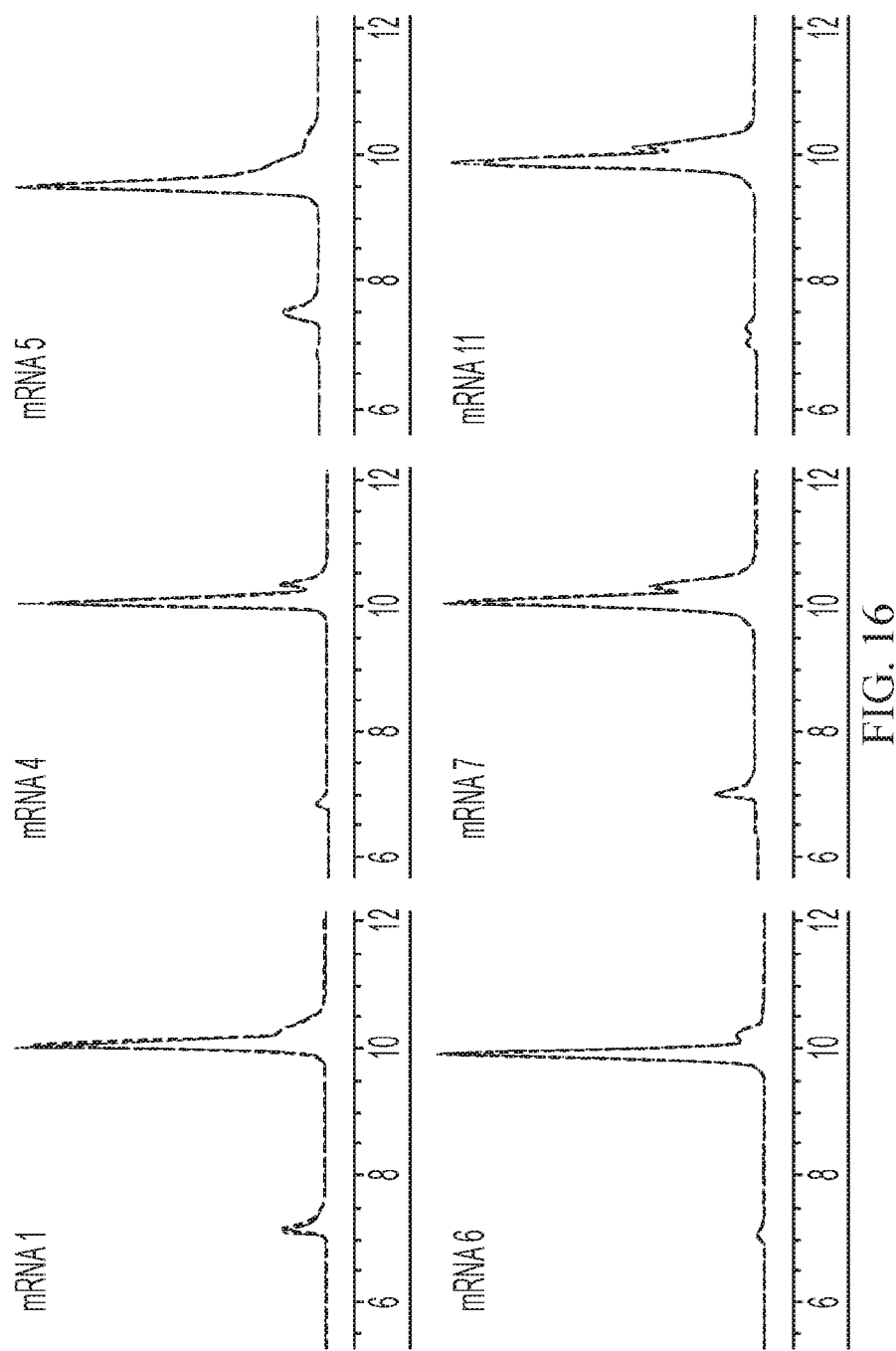
FIG. 16 shows representative data for the effect of sample pre-treatment on peak shape. Heat cycling the mRNA samples had no effect on peak splitting.

Thermal denaturing prior to analysis was investigated as a way to eliminate structure and peak splitting. This approach is effective at removing extraneous peaks in FA-CE, so the same conditions were applied: the diluted mRNA samples were heated to 75° C. for two minutes in a thermocycler, then snap-cooled to 4° C. Subsequent analysis of the subset of samples prone to peak splitting after heat cycling showed no difference compared to the control (FIG. 16). This, with the impact of column residence time and mobile phase concentration, suggests that to a large extent, the salt conditions in the method are creating and stabilizing the mRNA structure.

Figure 17:
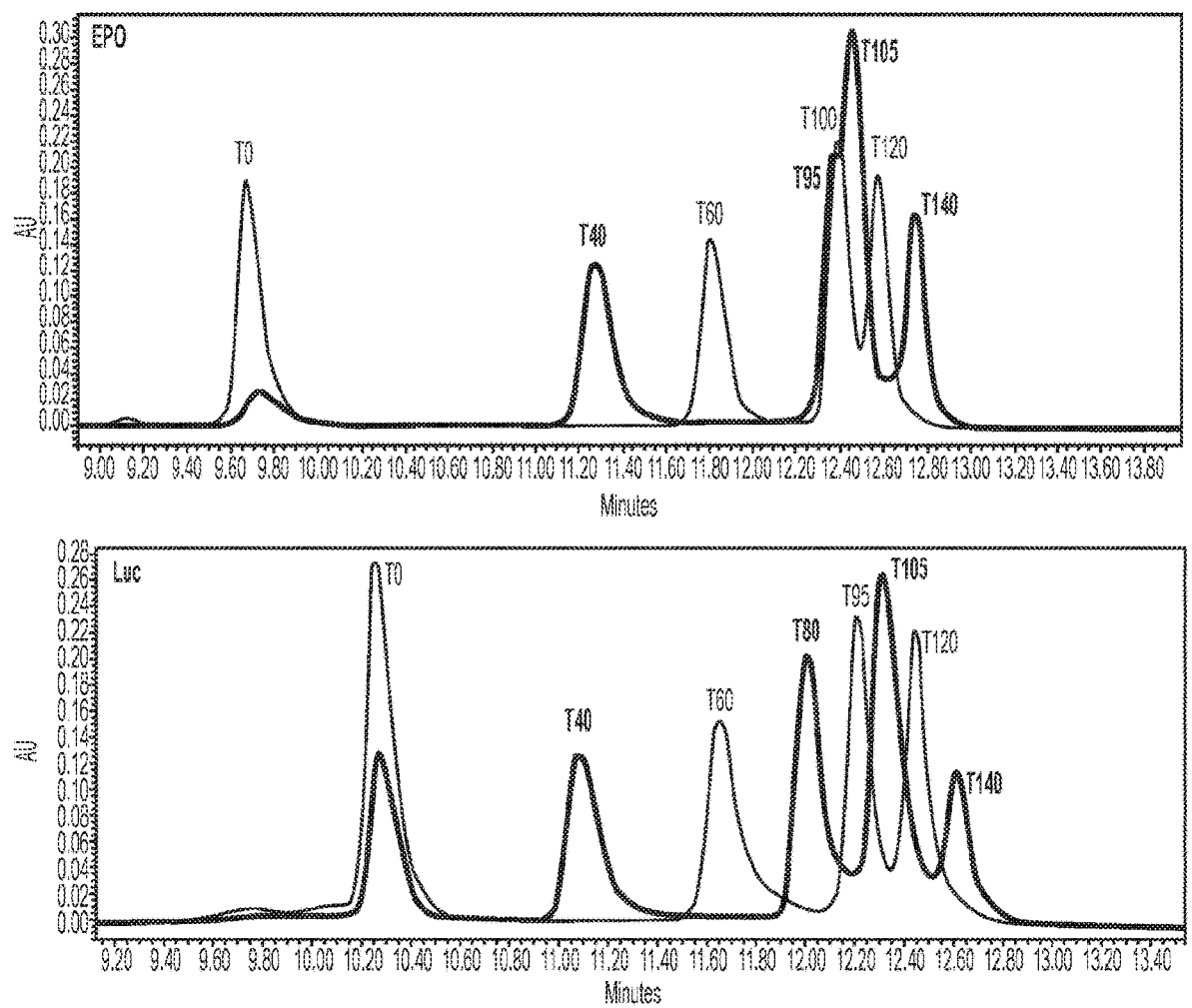
FIG. 17 shows representative data indicating that hEPO (top) and Luciferase (bottom) with tail length variants ranging from Tailless (T0) to a poly A tail length of 140As (T140) are well resolved using a HPLC methods as described by the disclosure.

An improved polyA tail-selective reversed phase HPLC method was developed for the detection and quantification of tailless RNA populations within a poly-adenylated mRNA preparation. FIG. 17 shows representative data indicating that hEPO (top) and Luciferase (bottom) with tail length variants ranging from Tailless (T0) to a poly A tail length of 140As (T140) are well resolved using a HPLC methods as described by the disclosure.

What is claimed is:

1. A method for separating a nucleic acid having a hydrophobic portion from a mixture comprising one or more additional nucleic acids or impurities, the method comprising:
   (i) contacting a hydrophobic stationary phase of a reverse phase chromatography column with the mixture; and
   (ii) eluting the nucleic acid having a hydrophobic portion with a mobile phase, wherein the mobile phase: (a) comprises an ion pairing agent selected from (i) Tris, (ii) inorganic cations, and (iii) biological buffers, and (b) lacks triethylammonium salts, tetrabutylammonium salts, hexylammonium salts, and dibutylammonium salts; such that the nucleic acid having a hydrophobic portion traverses the column with a retention time that is different than the one or more additional nucleic acids or impurities of the mixture.

2. The method of claim 1, wherein the column is an analytical column.

3. The method of claim 1, wherein the stationary phase comprises particles, wherein the particles
   (i) comprise an intrinsically hydrophobic material or comprise hydrophobic functional groups,
   (ii) are porous resin particles;
   (iii) have a diameter of about 2 µm-about 10 µm; and/or
   (iv) comprise pores having a diameter of about 500 Å to about 5000 Å.

4. The method of claim 1, wherein
   (i) the nucleic acid having a hydrophobic portion is mRNA;
   (ii) the hydrophobic portion comprises a polyA tail between about 10 and 500 adenosines in length, or wherein the hydrophobic portion comprises one or more hydrophobic base modifications; and/or
   (iii) the nucleic acid has a total length of between about 100 nucleotides and about 10,000 nucleotides.

5. The method of claim 1, wherein the mixture comprises
   (i) one or more tail length variants; and/or
   (ii) one or more degradation products.

6. The method of claim 1, wherein the mobile phase is
   (i) a single solvent; or
   (ii) a mixture of a first solvent and a second solvent.

7. The method of claim 6, wherein the mobile phase is a mixture of (i) a first solvent solution and (ii) a second solvent solution that is different from the first solvent solution.

8. The method of claim 7, wherein the first solvent solution and/or the second solvent solution comprises an ion pairing agent independently selected from (i) Tris, (ii) inorganic cations, and (iii) biological buffers.

9. The method of claim 7, wherein the first solvent solution and/or the second solvent solution further comprises a chelator.

10. The method of claim 7, wherein the first solvent solution and/or the second solvent solution comprises a solvent independently selected from water, polar aprotic solvents, $C_{1-4}$ alkanols, $C_{1-6}$ alkanediols, and $C_{2-4}$ alkanoic acids.

11. The method of claim 7, wherein
   (i) a pH of the first solvent solution is between about pH 6.8 and pH 8.5; and/or
   (ii) a pH of the second solvent solution is between about pH 6.8 and pH 8.5.

12. The method of claim 1, wherein the column has a temperature from about 70° C. to about 90° C.

13. The method of claim 1, wherein
   (i) the eluting is gradient with respect to mobile phase solvent composition;
   (ii) the eluting is isocratic with respect to a concentration of Tris in the mobile phase; and/or
   (iii) the method has a run time of between about 10 minutes and about 30 minutes.

14. The method of claim 1, wherein the method further comprises a step of detecting or isolating the nucleic acid having the hydrophobic portion.

15. The method of claim 1, wherein:
   (i) the inorganic cations are selected from Na, Li, K, and $NH_4$;
   (ii) the biological buffers are selected from MOPS, HEPES, and PIPES;
   (iii) the column has a temperature of about 80° C.; and/or
   (iv) the nucleic acid having a hydrophobic portion is an in vitro-transcribed (IVT) mRNA.

16. The method of claim 3, wherein the particles comprise polystyrene divinylbenzene.

17. The method of claim 7, wherein:
(i) the first solvent solution comprises an ion pairing agent selected from Tris, inorganic cations, and biological buffer, in a concentration of about 1 mM to about 200 mM;
(ii) the first solvent solution further comprises EDTA in a concentration from about 1 mM to about 5 mM;
(iii) the first solvent solution comprises one or more solvents selected from water, acetonitrile, methanol, ethanol, isopropanol, and hexylene glycol; and/or
(iv) a pH of the first solvent solution is about 7.0.

18. The method of claim 7, wherein:
(i) the second solvent solution comprises an ion pairing agent selected from Tris, inorganic cations, and biological buffers, in a concentration of about 1 mM to about 200 mM;
(ii) the second solvent solution further comprises EDTA in a concentration from about 1 mM to about 5 mM;
(iii) the second solvent solution comprises one or more solvents selected from water, acetonitrile, methanol, ethanol, isopropanol, and hexylene glycol; and/or
(iv) a pH of the second solvent solution is about 7.0.

19. The method of claim 7, wherein:
(i) each of the first and second solvent solutions comprises an ion pairing agent independently selected from Tris, inorganic cations, and biological buffers, in a concentration of about 1 mM to about 200 mM;
(ii) each of the first and second solvent solutions further comprises EDTA in a concentration from about 1 mM to about 5 mM;
(iii) each of the first and second solvent solutions comprises one or more solvents independently selected from water, acetonitrile, methanol, ethanol, isopropanol, and hexylene glycol; and/or
(iv) a pH of each of the first and second solvent solutions is between 6.8 and 8.5.

20. The method of claim 19, wherein:
(i) each of the first and second solvent solutions comprises Tris acetate in a concentration of about 1 mM to about 200 mM;
(ii) each of the first and second solvent solutions comprises EDTA in a concentration from about 1 mM to about 5 mM;
(iii) the first solvent solution comprises water and the second solvent solution comprises acetonitrile; and
(iii) a pH of each of the first and second solvent solutions is about 7.0.

* * * * *

UNITED STATES PATENT AND TRADEMARK OFFICE
CERTIFICATE OF CORRECTION

| | |
|---|---|
| PATENT NO. | : 11,912,982 B2 |
| APPLICATION NO. | : 16/639305 |
| DATED | : February 27, 2024 |
| INVENTOR(S) | : William Issa et al. |

It is certified that error appears in the above-identified patent and that said Letters Patent is hereby corrected as shown below:

In the Claims

Column 23, Line 6, Claim 17:
"buffer, in a concentration of about 1 mM to about 200"
Should read:
--buffers, in a concentration of about 1 mM to about 200--

Signed and Sealed this
Fourth Day of June, 2024

Katherine Kelly Vidal
*Director of the United States Patent and Trademark Office*